United States Patent
Kalnitsky et al.

(10) Patent No.: US 10,520,467 B2
(45) Date of Patent: Dec. 31, 2019

(54) CMOS COMPATIBLE BIOFET

(71) Applicant: Taiwan Semiconductor Manufacturing Co., Ltd., Hsinchu (TW)

(72) Inventors: Alexander Kalnitsky, San Francisco, CA (US); Yi-Shao Liu, Hsinchu County (TW); Kai-Chih Liang, Hsinchu County (TW); Chia-Hua Chu, Hsinchu County (TW); Chun-Ren Cheng, Hsin-Chu (TW); Chun-Wen Cheng, Hsinchu County (TW)

(73) Assignee: Taiwan Semiconductor Manufacturing Co., Ltd. (TW)

( * ) Notice: Subject to any disclaimer, the term of this patent is extended or adjusted under 35 U.S.C. 154(b) by 0 days.

(21) Appl. No.: 15/912,174

(22) Filed: Mar. 5, 2018

(65) Prior Publication Data
US 2018/0195998 A1    Jul. 12, 2018

Related U.S. Application Data

(60) Continuation of application No. 15/661,798, filed on Jul. 27, 2017, now Pat. No. 9,910,009, which is a
(Continued)

(51) Int. Cl.
*G01N 27/414* (2006.01)
*H01L 51/05* (2006.01)
(Continued)

(52) U.S. Cl.
CPC ....... *G01N 27/4145* (2013.01); *G01N 27/414* (2013.01); *G01N 27/4148* (2013.01);
(Continued)

(58) Field of Classification Search
CPC .............. H01L 51/0093; G01N 27/414; G01N 27/4145; G01N 27/4148
See application file for complete search history.

(56) References Cited

U.S. PATENT DOCUMENTS

| | | | |
|---|---|---|---|
| 4,225,875 A | 9/1980 | Ipri | |
| 4,468,574 A * | 8/1984 | Engeler | H01L 27/0928 257/371 |

(Continued)

FOREIGN PATENT DOCUMENTS

| | | |
|---|---|---|
| CN | 101553726 A | 10/2009 |
| CN | 102435653 A | 5/2012 |

(Continued)

OTHER PUBLICATIONS

Chung, Wen-Yaw et al., "A New Body-Effect Elimination Technique for ISFET Measurement," 2005 IEEE Sensors, Oct. 30, 2005-Nov. 3, 2005, pp. 1046-1049.
(Continued)

*Primary Examiner* — Mohsen Ahmadi
*Assistant Examiner* — Christopher M Roland
(74) *Attorney, Agent, or Firm* — Sterne, Kessler, Goldstein & Fox P.L.L.C.

(57) ABSTRACT

The present disclosure provides a bio-field effect transistor (BioFET) and a method of fabricating a BioFET device. The method includes forming a BioFET using one or more process steps compatible with or typical to a complementary metal-oxide-semiconductor (CMOS) process. The BioFET device may include a substrate; a gate structure disposed on a first surface of the substrate and an interface layer formed on the second surface of the substrate. The interface layer may allow for a receptor to be placed on the interface layer to detect the presence of a biomolecule or bio-entity.

20 Claims, 26 Drawing Sheets

Related U.S. Application Data continuation of application No. 15/284,283, filed on Oct. 3, 2016, now Pat. No. 9,791,406, which is a division of application No. 13/480,161, filed on May 24, 2012, now Pat. No. 9,459,234.

(60) Provisional application No. 61/553,606, filed on Oct. 31, 2011.

(51) Int. Cl.
*H01L 51/00* (2006.01)
*H01L 21/84* (2006.01)
*H01L 27/12* (2006.01)

(52) U.S. Cl.
CPC .......... *H01L 21/84* (2013.01); *H01L 27/1203* (2013.01); *H01L 51/0093* (2013.01)

(56) References Cited

U.S. PATENT DOCUMENTS

| | | | |
|---|---|---|---|
| 5,321,293 | A | 6/1994 | Mojardi et al. |
| 5,702,981 | A | 12/1997 | Maniar et al. |
| 7,060,510 | B2 | 6/2006 | Bonnell et al. |
| 7,306,924 | B2 | 12/2007 | Gomez et al. |
| 7,632,670 | B2 | 12/2009 | Offenhausser et al. |
| 7,695,609 | B2 | 4/2010 | Soundarrajan et al. |
| 7,696,530 | B2 | 4/2010 | Yamamoto et al. |
| 7,772,617 | B2 | 8/2010 | Fleischer et al. |
| 7,833,708 | B2 | 11/2010 | Enzelberger et al. |
| 7,902,089 | B2 | 3/2011 | Matsumoto et al. |
| 7,923,314 | B2 | 4/2011 | Tezuka et al. |
| 7,939,449 | B2 | 5/2011 | Cobbley et al. |
| 8,007,727 | B2 | 8/2011 | Shalev et al. |
| 8,154,093 | B2 | 4/2012 | Bradley et al. |
| 8,420,328 | B2 | 4/2013 | Chen et al. |
| 8,471,559 | B2 | 6/2013 | Taherian et al. |
| 8,519,490 | B2 | 8/2013 | Bikumandla et al. |
| 8,557,643 | B2 | 10/2013 | Han et al. |
| 8,728,844 | B1 | 5/2014 | Liu et al. |
| 8,778,269 | B2 | 7/2014 | Joshi et al. |
| 8,859,316 | B2 | 10/2014 | Guo et al. |
| 8,871,549 | B2 | 10/2014 | Ellis-Monaghan et al. |
| 8,878,258 | B2 | 11/2014 | Monfray et al. |
| 8,900,905 | B1 | 12/2014 | Liu et al. |
| 9,080,969 | B2 | 7/2015 | Liu et al. |
| 9,389,199 | B2 | 7/2016 | Cheng et al. |
| 9,417,209 | B2 | 8/2016 | Shen et al. |
| 9,459,234 | B2 | 10/2016 | Kalnitsky et al. |
| 9,689,835 | B2 | 6/2017 | Liu et al. |
| 9,791,406 | B2 | 10/2017 | Kalnitsky et al. |
| 9,910,009 | B2 | 3/2018 | Kalnitsky et al. |
| 9,958,443 | B2 | 5/2018 | Lin et al. |
| 10,094,801 | B2 | 10/2018 | Liu et al. |
| 2002/0006632 | A1 | 1/2002 | Ponnampalam et al. |
| 2002/0127623 | A1 | 9/2002 | Minshull et al. |
| 2004/0132070 | A1 | 7/2004 | Star et al. |
| 2004/0238379 | A1 | 12/2004 | Lindsay et al. |
| 2005/0053524 | A1 | 3/2005 | Keersmaecker et al. |
| 2005/0156207 | A1 | 7/2005 | Yazawa et al. |
| 2006/0102935 | A1 | 5/2006 | Yitzchaik et al. |
| 2006/0246478 | A1 | 11/2006 | Yoo et al. |
| 2006/0278528 | A1 | 12/2006 | Fleischer et al. |
| 2007/0132043 | A1* | 6/2007 | Bradley ................ B82Y 10/00 257/414 |
| 2007/0295988 | A1 | 12/2007 | Yamamoto et al. |
| 2008/0069971 | A1* | 3/2008 | Keersmaecker ....... B82Y 15/00 427/555 |
| 2009/0294805 | A1* | 12/2009 | Shalev ............... G01N 33/5438 257/253 |
| 2009/0294983 | A1* | 12/2009 | Cobbley .......... H01L 21/76898 257/774 |
| 2010/0055699 | A1 | 3/2010 | Kahya |
| 2010/0198521 | A1 | 8/2010 | Haick et al. |
| 2010/0273672 | A1 | 10/2010 | Demoustier-Champagne et al. |
| 2011/0019488 | A1 | 1/2011 | Yamamoto et al. |
| 2012/0021918 | A1 | 1/2012 | Bashir et al. |
| 2012/0045368 | A1 | 2/2012 | Hinz et al. |
| 2012/0223436 | A1* | 9/2012 | Sekar .................... H01L 23/367 257/773 |
| 2013/0105868 | A1 | 5/2013 | Kalnitsky et al. |
| 2013/0200438 | A1 | 8/2013 | Liu et al. |
| 2013/0291627 | A1 | 11/2013 | Hu et al. |
| 2014/0073039 | A1 | 3/2014 | Chang et al. |
| 2014/0151755 | A1 | 6/2014 | Liu et al. |
| 2014/0252421 | A1 | 9/2014 | Liu et al. |
| 2014/0256030 | A1 | 9/2014 | Shen et al. |
| 2014/0264468 | A1 | 9/2014 | Cheng et al. |
| 2014/0295573 | A1 | 10/2014 | Huang et al. |
| 2014/0308752 | A1 | 10/2014 | Chang et al. |

FOREIGN PATENT DOCUMENTS

| | | |
|---|---|---|
| TW | 201224478 | 6/2012 |
| WO | WO 2010/037085 A1 | 4/2010 |

OTHER PUBLICATIONS

Kalnitsky, Alexander et al, "CMOS Compatible BioFET," U.S. Appl. No. 61/553,606, filed Oct. 31, 2011, 26 pages.

Merriman, Barry, Ion Torrent R&D Team, Jonathan M. Rothberg, "Progress in Ion Torrent Semiconductor Chip Based Sequencing," Electrophoresis 2012, 33, 3397-3417.

J. Go, P. R. Nair, B. Reddy Jr., B. Dorvel, R. Bashir, and M.A. Alam, "Coupled Heterogeneous 'Nanowire-Nanoplate' Planar Transistor Sensors for Giant (>1 OV/pH) Nernst Response," ACS Nano, vol. 6, No. 7, 5972-5979, 2012.

Heitzinger et al., "Modeling and Simulation of Field-Effect Biosensors (BioFETs) and their Deployment on the NanoHUB," 2008, Journal of Physics: Conference Series 107 (2008) 012004; pp. 1-12; Physics-Based Mathematical Models of Low-Dimensional Semiconductor Nanostructures; IOP Publishing Ltd.; http://iopscience.iop.org/1742-6596/107/1/012004.

Michael J. Schoning and Arshak Poghossian, "Recent Advances in Biologically Sensitive Field Effect Transistors (BioFETs)," Aug. 16, 2002, 15 pages, a) University of Applied Sciences Aachen, Ginsterweg 1, D-52428 Jülich, Germany; b) Institute of Thin Films and Interfaces, Research Centre Jülich GmbH, D-52425 Jülich, Germany.

Jeho Park, et al., "Applications of Field-Effect Transistor (FET)-Type Biosensors," Applied Science and Convergence Technology, vol. 23 No. 2, Mar. 2014; pp. 61-71.

Huang, et al., "High Performance Dual-Gate ISFET with Non-Ideal Effect Reduction Schemes in a SOI-CMOS Bioelectrical SoC," 2015 IEEE International Electron Devices Meeting (IEDM), Dec. 2015, Taiwan Semiconductor Manufacturing Company (TSMC), Hsinchu, Taiwan, pp. 29-2.1-29.2.4 (4 pages).

\* cited by examiner

CMOS COMPATIBLE BIOFET

PRIORITY DATA

The present application is a continuation of U.S. patent application Ser. No. 15/661,798, filed Jul. 27, 2017, entitled "CMOS COMPATIBLE BIOFET," which is a continuation of U.S. patent application Ser. No. 15/284,283, filed Oct. 3, 2016, entitled "CMOS COMPATIBLE BIOFET," which is a divisional application of U.S. patent application Ser. No. 13/480,161, filed May 24, 2012, entitled "CMOS COMPATIBLE BIOFET," which claims priority to Provisional Application Ser. No. 61/553,606, filed on Oct. 31, 2011, entitled "CMOS COMPATIBLE BIOFET," each of which is hereby incorporated by reference in its entirety.

BACKGROUND

Biosensors are devices for sensing and detecting biomolecules and operate on the basis of electronic, electrochemical, optical, and mechanical detection principles. Biosensors that include transistors are sensors that electrically sense charges, photons, and mechanical properties of bio-entities or biomolecules. The detection can be performed by detecting the bio-entities or biomolecules themselves, or through interaction and reaction between specified reactants and bio-entities/biomolecules. Such biosensors can be manufactured using semiconductor processes, can quickly convert electric signals, and can be easily applied to integrated circuits (ICs) and MEMS.

BioFETs (biologically sensitive field-effect transistors, or bio-organic field-effect transistors) are a type of biosensor that includes a transistor for electrically sensing biomolecules or bio-entities. While BioFETs are advantageous in many respects, challenges in their fabrication and/or operation arise, for example, due to compatibility issues between the semiconductor fabrication processes, the biological applications, restrictions and/or limits on the semiconductor fabrication processes, integration of the electrical signals and biological applications, and/or other challenges arising from implementing a large scale integration (LSI) process.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
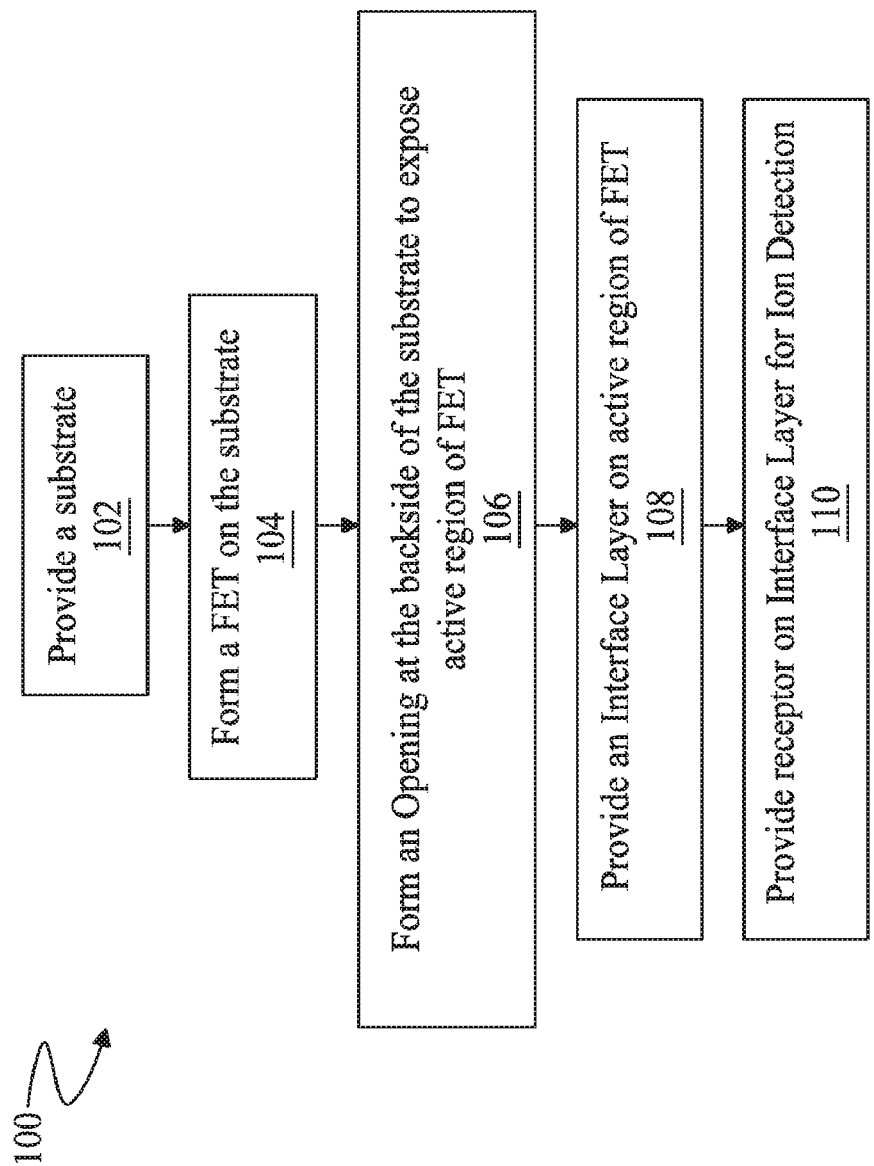
FIG. 1 is a flow chart of an embodiment of a method of fabricating a BioFET device according to one or more aspects of the present disclosure.

It is to be understood that the following disclosure provides many different embodiments, or examples, for implementing different features of the invention. Specific examples of components and arrangements are described below to simplify the present disclosure. These are, of course, merely examples and are not intended to be limiting. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Further still, references to relative terms such as "top", "front", "bottom", and "back" are used to provide a relative relationship between elements and are not intended to imply any absolute direction. Various features may be arbitrarily drawn in different scales for simplicity and clarity.

In a BioFET, the gate of a MOSFET (metal-oxide-semiconductor field-effect transistor), which controls the conductance of the semiconductor between its source and drain contacts, is replaced by a bio- or biochemical-compatible layer or a biofunctionalized layer of immobilized probe molecules that act as surface receptors. Essentially, a BioFET is a field-effect biosensor with a semiconductor transducer. A decided advantage of BioFETs is the prospect of label-free operation. Specifically, BioFETs enable the avoidance of costly and time-consuming labeling operations such as the labeling of an analyte with, for instance, fluorescent or radioactive probes.

A typical detection mechanism for BioFETs is the conductance modulation of the transducer due to the binding of a target biomolecule or bio-entity to the gate or a receptor molecule immobilized on the gate of the BioFET. When the target biomolecule or bio-entity is bonded to the gate or the immobilized receptor, the drain current of the BioFET is varied by the gate potential. This change in the drain current can be measured and the bonding of the receptor and the target biomolecule or bio-entity can be identified. A great variety of biomolecules and bio-entities may be used to functionalize the gate of the BioFET such as ions, enzymes, antibodies, ligands, receptors, peptides, oligonucleotides, cells of organs, organisms and pieces of tissue. For instance, to detect ssDNA (single-stranded deoxyribonucleic acid), the gate of the BioFET may be functionalized with immobilized complementary ssDNA strands. Also, to detect various proteins such as tumor markers, the gate of the BioFET may be functionalized with monoclonal antibodies.

One example of a typical biosensor is an ion-sensitive field effect transistor (ISFET) device. While suitable for some purposes, the ISFET has disadvantages. Its construction requires removal of the conductive gate material from the transistor and thus, exposure of the gate dielectric to the surrounding environment where potential-modulating surface reactions may occur. The ISFET device is also challenging to construct due to the multiple levels of metal interconnect layers.

Another device structure that may be formed includes connecting a gate structure with the surrounding environment though a stack of metal interconnect lines and vias (or multi-layer interconnect, MLI). In such an embodiment, the potential-modulating reaction takes place at an outer surface of the final (top) metal layer or a dielectric surface formed on top of the MLI. This embodiment may be disadvantageous however, in that the sensitivity of the device may be decreased due to the presence of parasitic capacitances associated with the MLI.

Figure 5:
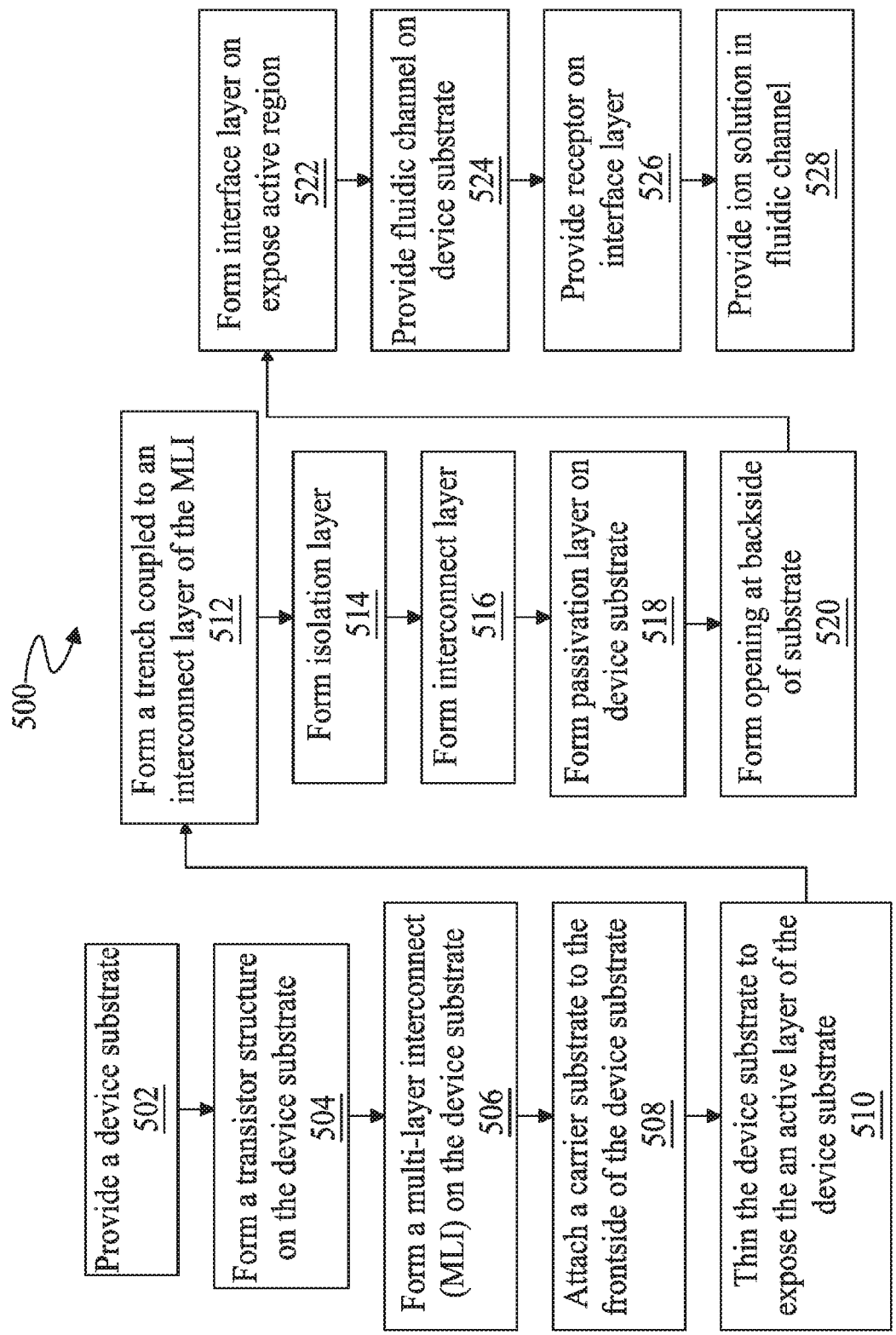
FIG. 5 is a flow chart of a method of fabricating a BioFET device using complementary metal oxide semiconductor (CMOS) compatible process(es).
Figure 18:
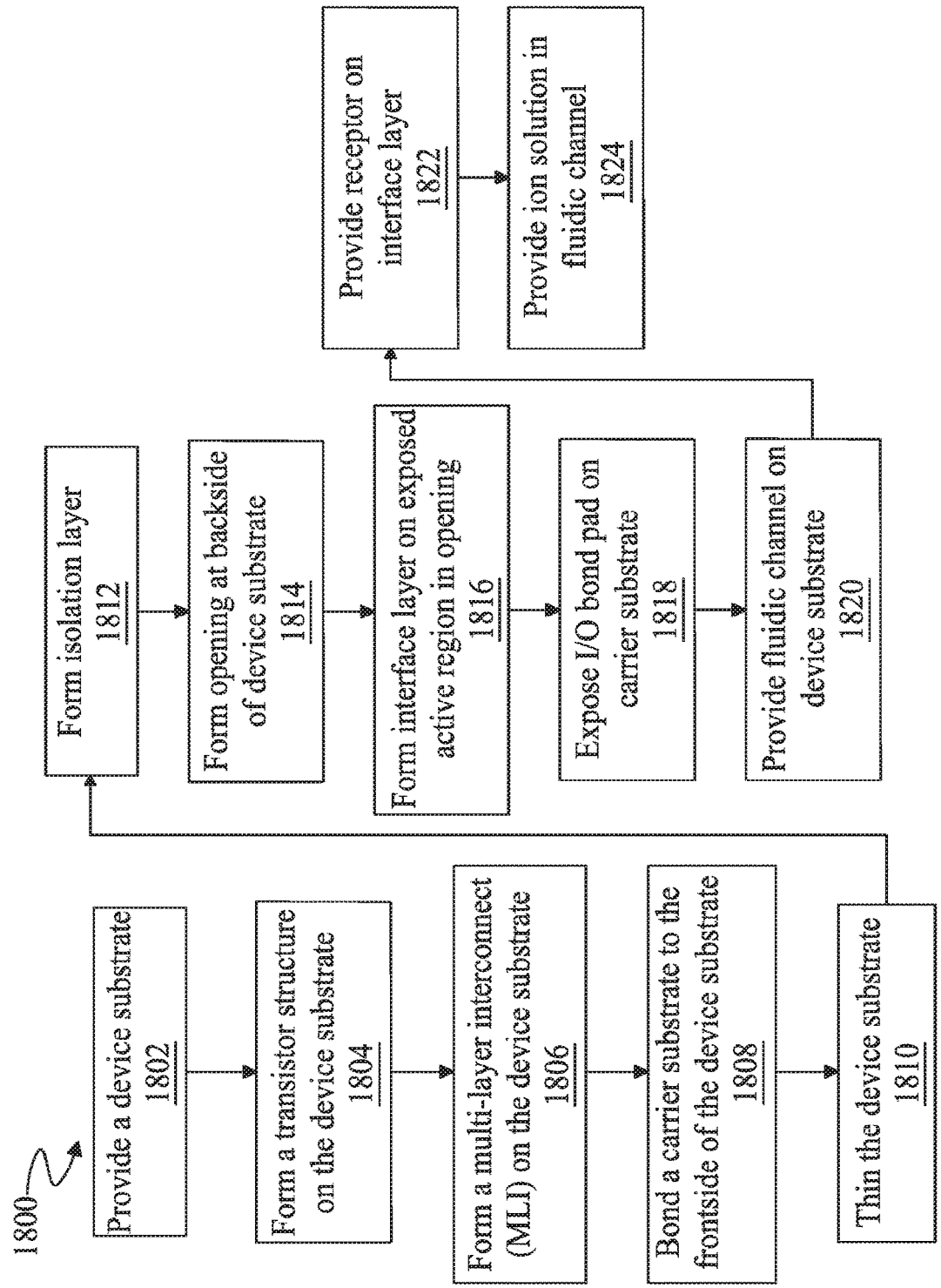
FIG. 18 is a flow chart of another method of fabricating a BioFET device using complementary metal oxide semiconductor (CMOS) compatible process(es).

Illustrated in FIG. 1 is an embodiment of a method 100 of fabricating a bio-organic field effect transistor (BioFET). The method 100 may include forming a BioFET using one or more process steps compatible with or typical to a complementary metal-oxide-semiconductor (CMOS) process. It is understood that additional steps can be provided before, during, and after the method 100, and some of the steps described below can be replaced or eliminated, for additional embodiments of the method. Further, it is understood that the method 100 includes steps having features of a typical CMOS technology process flow and thus, are only described briefly herein. It is also noted that FIGS. 5 and 18 provide further embodiments of the method 100, which may provide additional details applicable to the method 100.

The method 100 begins at block 102 where a substrate is provided. The substrate may be a semiconductor substrate (e.g., wafer). The semiconductor substrate may be a silicon substrate. Alternatively, the substrate may comprise another elementary semiconductor, such as germanium; a compound semiconductor including silicon carbide, gallium arsenic, gallium phosphide, indium phosphide, indium arsenide, and/or indium antimonide; an alloy semiconductor including SiGe, GaAsP, AlInAs, AlGaAs, GaInAs, GaInP, and/or GaInAsP; or combinations thereof. In an embodiment, the substrate is a semiconductor on insulator (SOI) substrate. The SOI substrate may include a buried oxide (BOX) layer formed by a process such as separation by implanted oxygen (SIMOX), and/or other suitable processes. The substrate may include doped regions, such as p-wells and n-wells.

The method 100 then proceeds to block 104 where a field effect transistor (FET) is formed on the substrate. The FET may include a gate structure, a source region, a drain region, and a channel region interposing the source and drain regions. The source, drain, and/or channel region may be formed on an active region of the semiconductor substrate. The FET may be an n-type FET (nFET) or a p-type FET (pFET). For example, the source/drain regions may comprise n-type dopants or p-type dopants depending on the FET configuration. The gate structure may include a gate dielectric layer, a gate electrode layer, and/or other suitable layers. In an embodiment, the gate electrode is polysilicon. Other exemplary gate electrodes include metal gate electrodes including material such as, Cu, W, Ti, Ta, Cr, Pt, Ag, Au; suitable metallic compounds like TiN, TaN, NiSi, CoSi; combinations thereof; and/or other suitable conductive materials. In an embodiment, the gate dielectric is silicon oxide. Other exemplary gate dielectrics include silicon nitride, silicon oxynitride, a dielectric with a high dielectric constant (high k), and/or combinations thereof. Examples of high k materials include hafnium silicate, hafnium oxide, zirconium oxide, aluminum oxide, tantalum pentoxide, hafnium dioxide-alumina ($HfO_2$—$Al_2O_3$) alloy, or combinations thereof. The FET may be formed using typical CMOS processes such as, photolithography; ion implantation; diffusion; deposition including physical vapor deposition (PVD), metal evaporation or sputtering, chemical vapor deposition (CVD), plasma-enhanced chemical vapor deposition (PECVD), atmospheric pressure chemical vapor deposition (APCVD), low-pressure CVD (LPCVD), high density plasma CVD (HDPCVD), atomic layer CVD (ALCVD), spin on coating; etching including wet etching, dry etching, and plasma etching; and/or other suitable CMOS processes.

The method 100 then proceeds to block 106 where an opening is formed at the backside of the substrate. The opening may include a trench formed in one or more layers disposed on the backside of the substrate that includes the FET device. The opening may expose a region underlying the gate and body structure (e.g., adjacent the channel of the FET). In an embodiment, the opening exposes an active region (e.g., silicon active region) underlying the gate and active/channel region of the FET device. The opening may be formed using suitable photolithography processes to provide a pattern on the substrate and etching process to remove materials form the backside till the body structure of the FET device exposed. The etching processes include wet etch, dry etch, plasma etch and/or other suitable processes.

The method 100 then proceeds to block 108 where an interface layer is formed in the opening. The interface layer may be formed on the exposed active region underlying the gate structure of the FET. The interface layer may be compatible (e.g., friendly) for biomolecules or bio-entities binding. For example, the interface layer may provide a binding interface for biomolecules or bio-entities. The interface layer may include a dielectric material, a conductive material, and/or other suitable material for holding a receptor. Exemplary interface materials include high-k dielectric films, metals, metal oxides, dielectrics, and/or other suitable materials. As a further example, exemplary interface materials include $HfO_2$, $Ta_2O_5$, Pt, Au, W, Ti, Al, Cu, oxides of such metals, $SiO_2$, $Si_3N_4$, $Al_2O_3$, $TiO_2$, TiN, SnO, $SnO_2$; and/or other suitable materials. The interface layer may be formed using CMOS processes such as, for example, physical vapor deposition (PVD) (sputtering), chemical vapor deposition (CVD), plasma-enhanced chemical vapor deposition (PECVD), atmospheric pressure chemical vapor deposition (APCVD), low-pressure CVD (LPCVD), high density plasma CVD (HDPCVD), or atomic layer CVD (ALCVD). In embodiments, the interface layer includes a plurality of layers.

The method 100 then proceeds to block 110 where a receptor such as an enzyme, antibody, ligand, peptide, nucleotide, cell of an organ, organism or piece of tissue is placed on an interface layer for detection of a target biomolecule.

Figure 2:
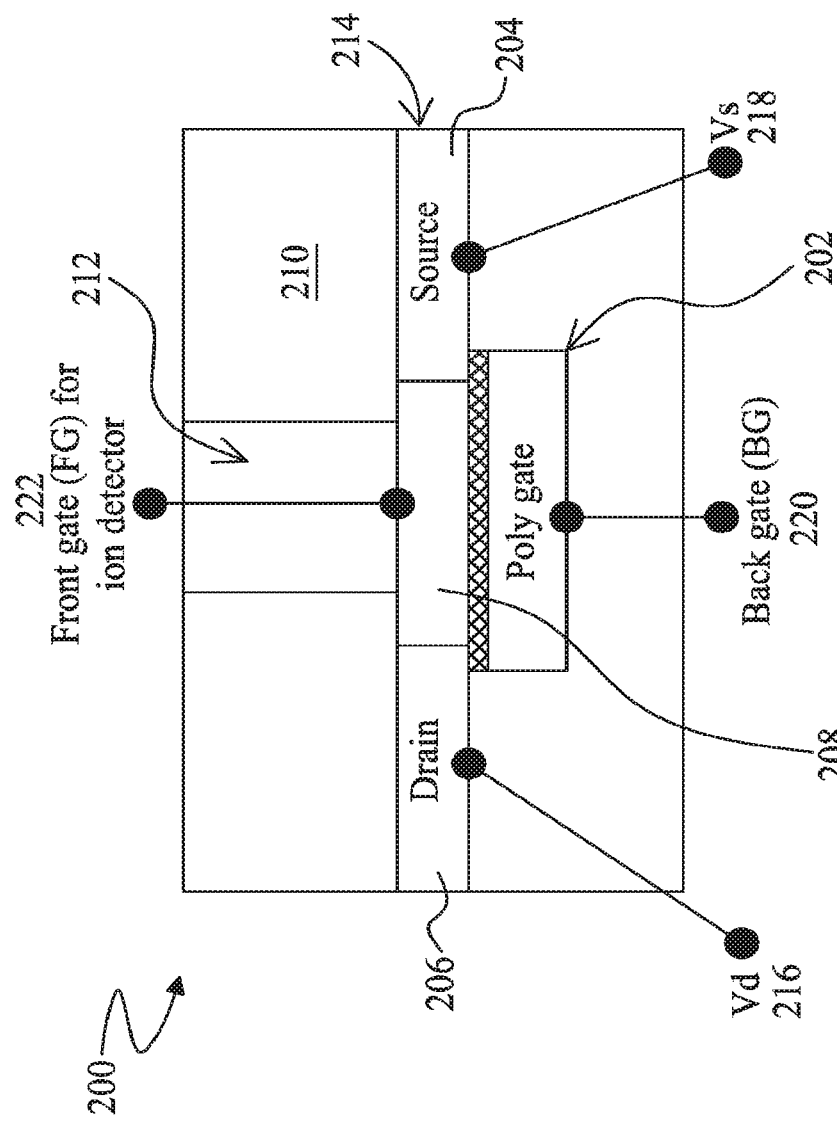
FIG. 2 is a cross-sectional view of an embodiment of a BioFET device according to one or more aspects of the present disclosure.

Referring now to FIG. 2, illustrated is a semiconductor device 200. The semiconductor device 200 may be a BioFET device. The semiconductor device 200 may be formed using one or more aspects of the method 100, described above with reference to FIG. 1.

The semiconductor device 200 includes a gate structure 202 formed on substrate 214. The substrate 214 further includes a source region 204, a drain region 206, and an active region 208 (e.g., including a channel region) interposing the source region 204 and the drain region 206. The gate structure 202, the source region 204, the drain region 206, and the active region 208 may be formed using suitable CMOS process technology. The gate structure 202, the source region 204, the drain region 206, and the active region 208 form a FET. An isolation layer 210 is disposed on the opposing side of the substrate 214, as compared to the gate structure 202 (i.e., backside of the substrate).

An opening 212 is provided in the isolation layer 210. The opening 212 is substantially aligned with the gate structure 202. As described above with reference to block 108 of the method 100 of FIG. 1, an interface layer may be disposed in the opening 212 on the surface of the active region 208. The interface layer may be operable to provide an interface for positioning one or more receptors for detection of biomolecules or bio-entities.

The semiconductor device 200 includes electrical contacts to the source region 206 (Vd 216), the drain region (Vs 218), the gate structure 202 (back gate (BG) 220), and/or the active region 208 (e.g., front gate (FG) 222).

Thus, while a conventional FET uses a gate contact to control conductance of the semiconductor between the source and drain (e.g., the channel), the semiconductor device 200 allows receptors formed on the opposing side of the FET device to control the conductance, while the gate structure 202 (e.g., polysilicon) provides a back gate (e.g., source substrate or body node in a conventional FET). The gate structure 202 provides a back gate that can control the channel electron distribution without a bulk substrate effect. Thus, if the receptors attach to a molecule provided on an interface layer in the opening 212, the resistance of the field-effect transistor channel in the active region 208 is altered. Therefore, the semiconductor device 200 may be used to detect one or more specific biomolecules or bio-entities in the environment around and/or in the opening 212.

The semiconductor device 200 may include additional passive components such as resistors, capacitors, inductors, and/or fuses; and other active components, including P-channel field effect transistors (PFETs), N-channel field effect transistors (NFETs), metal-oxide-semiconductor field effect transistors (MOSFETs), complementary metal-oxide-semiconductor (CMOS) transistors, high voltage transistors, and/or high frequency transistors; other suitable components; and/or combinations thereof. It is further understood that additional features can be added in the semiconductor device 200, and some of the features described below can be replaced or eliminated, for additional embodiments of the semiconductor device 200.

Figure 3:
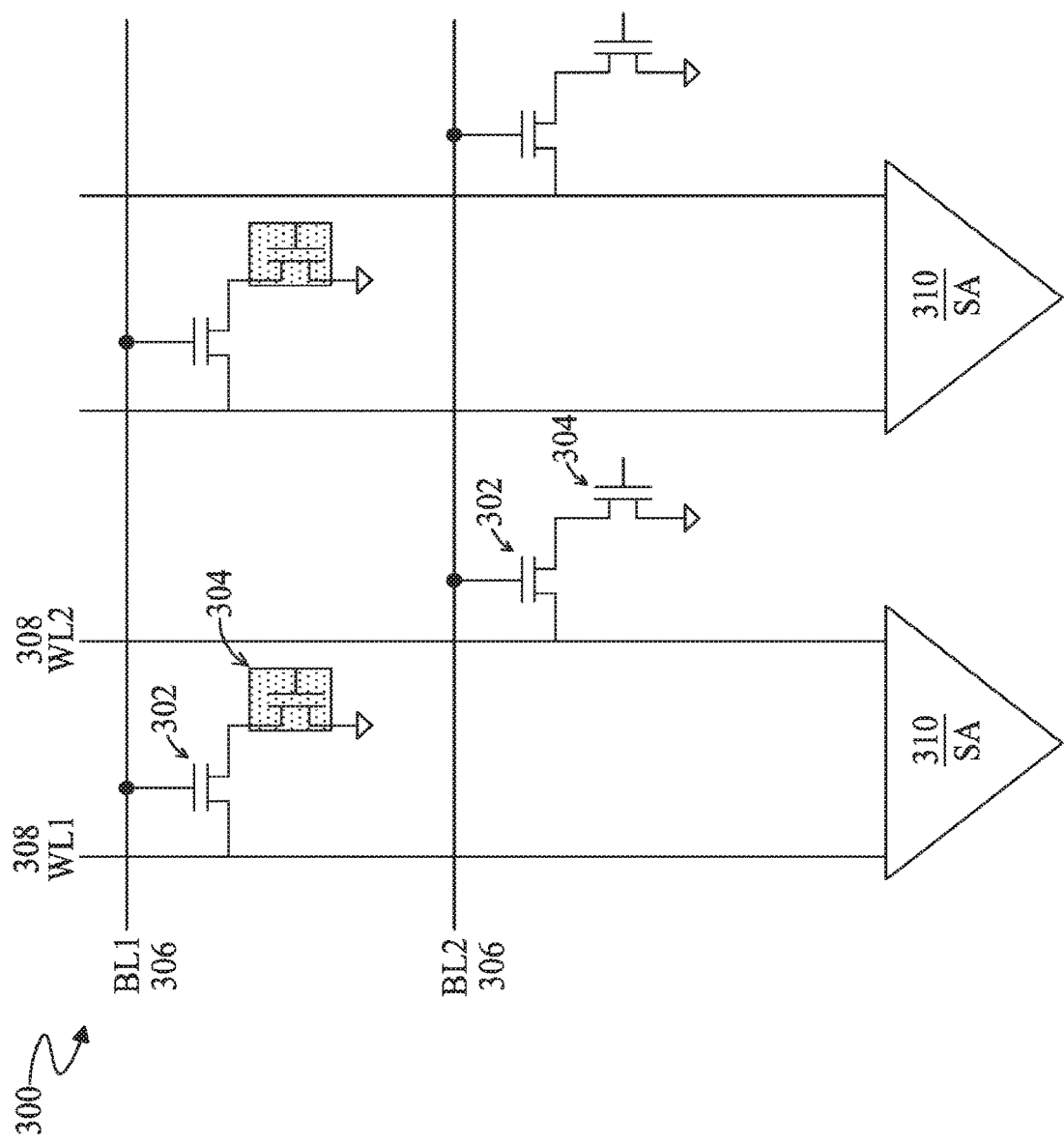
FIG. 3 is a circuit diagram of an embodiment of a plurality of BioFET devices configured in an array arrangement according to one or more aspects of the present disclosure.

Referring now to FIG. 3, illustrated a schematic of a layout 300 of a plurality of semiconductor devices 302 and 304 connected to bit lines 306 and word lines 308. (It is noted that the terms bit lines and word lines are used herein to indicate similarities to array construction in memory devices, however, there is no implication that memory devices or a storage array necessarily be included in the array. However, the layout 300 may have similarities to that employed in other semiconductor devices such as dynamic random access memory (DRAM) arrays. For example, a BioFET such as the semiconductor device 200, described above with reference to FIG. 2, may be formed in a position a capacitor would be found in a traditional DRAM array.) The schematic 300 is exemplary only and one would recognize other configurations are possible.

The semiconductor devices 304 include BioFET devices. The semiconductor devices 304 may be substantially similar to the semiconductor device 200, described above with reference to FIG. 2. The semiconductor devices 302 may include transistors (e.g. control transistors or switching elements) operable to provide connection to the semiconductor device 304 (e.g., BioFET). The semiconductor devices 304 may include a front gate provided by a receptor material formed on a frontside of the FET and a back gate provided by a gate structure (e.g., polysilicon).

The schematic 300 includes an array formation that may be advantageous in detecting small signal changes provided by minimal biomolecules or bio-entities introduced to the semiconductor devices 304. Further, this may be accomplished by using a decreased number of input/output pads. The schematic 300 includes sense amplifies 310. The sense amplifiers 310 may enhance the signal quality and magnification to improve the detection ability of the device having the layout 300. In an embodiment, when particular lines 306 and lines 308 are turned on, the corresponding semiconductor device 302 will be turned on, thus allowing the corresponding semiconductor device 302 to function as in ON-state. When the gate of the associated semiconductor device 304 (e.g., front gate such as gate structure 222 of the semiconductor device 200) is triggered by the bio-molecule presence, the semiconductor device 304 will transfer electrons and induce the field effect charging of the device, thereby modulating the current (e.g., Ids). The change of the current (e.g., Ids) or threshold voltage (Vt) can serve to indicate detection of the relevant biomolecules or bio-entities. Thus, the device having the schematic 300 can achieve a biosensor application including application with differential sensing for enhanced sensitivity.

Figure 4:
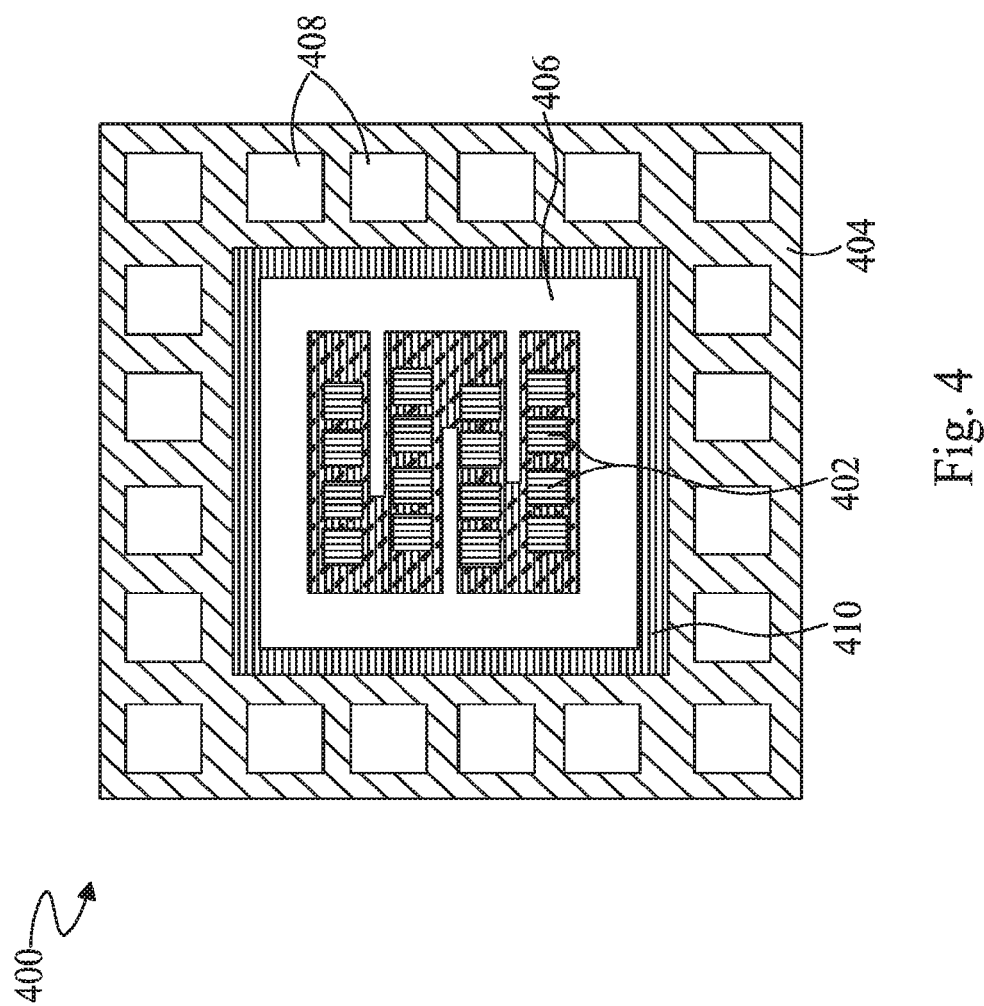
FIG. 4 is a top view of an embodiment of a device including a plurality of BioFET devices formed according to one or more aspects of the present disclosure.
Figure 26:
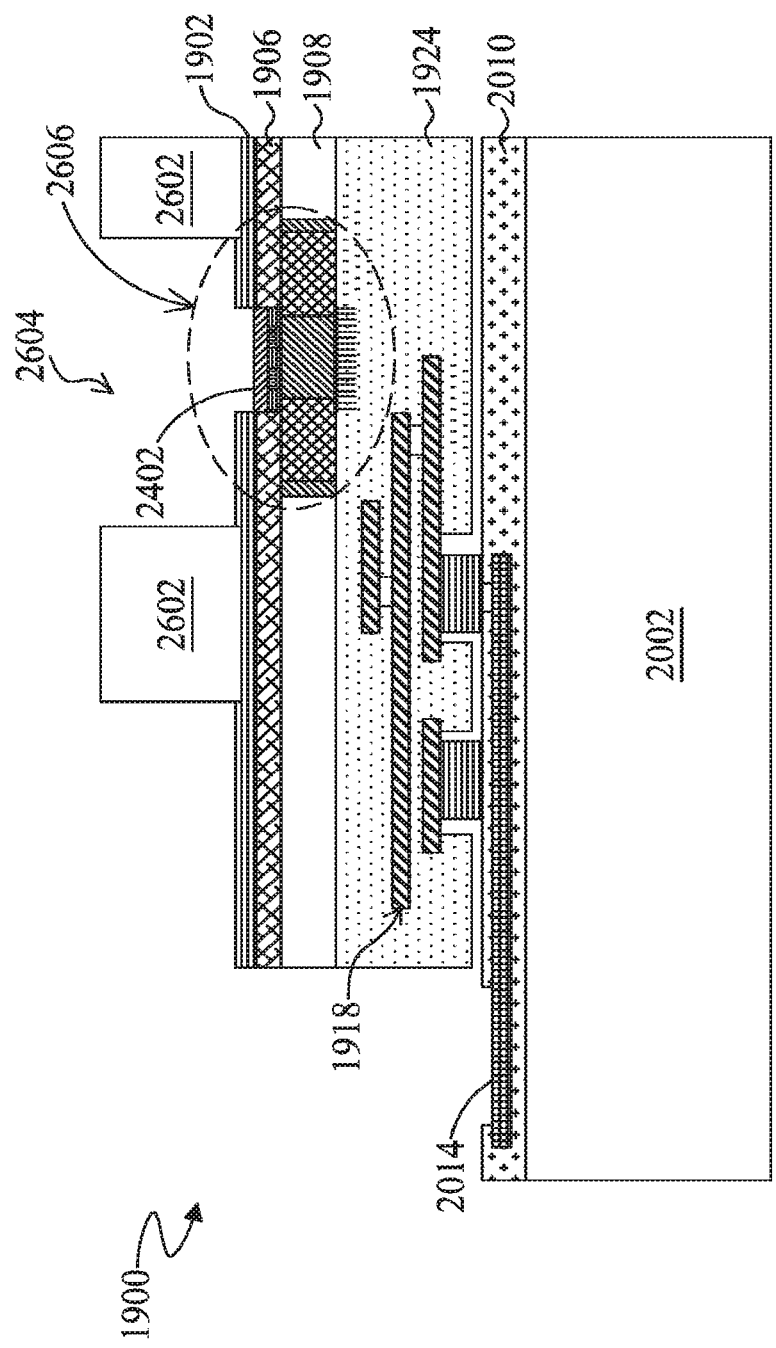

Referring now to FIG. 4, illustrated is a top-view of a semiconductor device 400 for bio-sensing applications. The semiconductor device 400 includes a plurality of BioFETs disposed on a substrate 404. In an embodiment, the semiconductor device 400 may include a layout substantially similar to the layout 300, described above with reference to FIG. 3. The substrate 404 may be a semiconductor substrate and/or a carrier substrate such as discussed with reference to FIG. 1 above, and/or with reference to the detailed description below. The BioFETs may be substantially similar to the semiconductor device 200, described above with reference to FIG. 2, the BioFET 1704, described below with reference to FIG. 17, and/or the BioFET 2606, described below with reference to FIG. 26. An opening is provided in the BioFET devices, such as discussed above with reference to the opening 212 of the semiconductor device 200; this opening may be illustrated as element 402. The opening may also be referred to as a front-gate opening well 402.

A fluidic channel 406 is disposed on the substrate 404. The fluidic channel 406 may provide a channel or container (e.g., reservoir) operable to hold and/or direct a fluid. In an embodiment, the fluidic channel 406 includes polydimethylsiloxane (PDMS) elastomer. However, other embodiments are possible. Typically, the fluidic channel 406 may be fabricated and/or connected or bonded to the device 400 outside of a CMOS process, for example, the fluidic channel 406 may be fabricated and/or connected to the device 400 using processes that are not typical of standard CMOS fabrication. In an embodiment a second entity, separate from the entity fabricating the transistors, may connect the fluidic channel to the substrate 404. The fluid being utilized may be a chemical solution. The fluid may contain target biomolecules or bio-entities.

Peripheral circuitry region 410 surrounds the BioFETs. The peripheral circuitry region 410 may include circuitry to drive and/or sense the variations in the BioFET devices, e.g., including front-gate opening wells 402. The peripheral circuitry may include additional passive components such as resistors, capacitors, inductors, and/or fuses; and other active components, including P-channel field effect transistors (PFETs), N-channel field effect transistors (NFETs), metal-oxide-semiconductor field effect transistors (MOS- FETs), complementary metal-oxide-semiconductor transistors (CMOSs), high voltage transistors, and/or other suitable devices.

Figure 12:
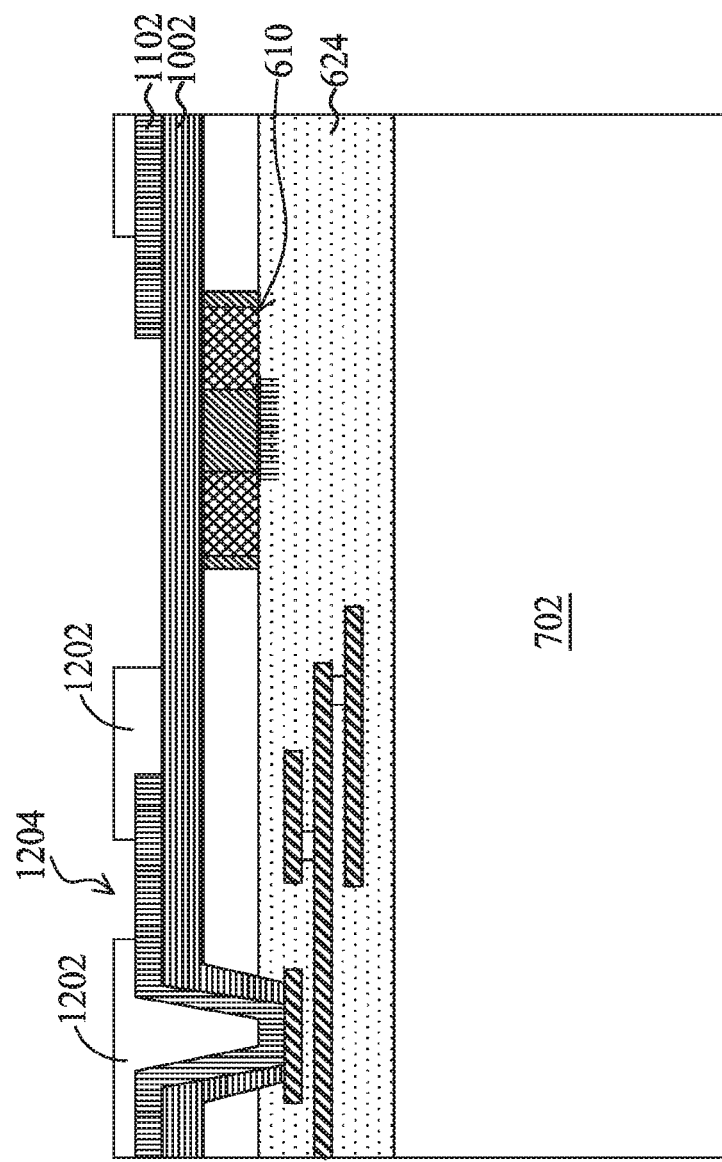

A plurality of bond pads 408 is disposed on the substrate 404. The bond pads 408 may include conductive landings operable to provide a region for wire bonding, ball or bump bonding, and/or other bonding techniques. The bond pads 408 are operable to provide physical and/or electrical connection to other semiconductor devices and/or instrumentations. The bond pads 408 may include any suitable structural material, including copper, aluminum, titanium, tungsten, alloys thereof, composites thereof, combinations thereof, and/or other suitable materials. The bond pads 408 may be substantially similar to the opening 1204 that exposes a conductive pad, described below with reference to FIG. 12 and/or the I/O pad 2014 described below with reference to FIG. 20.

Referring now to FIG. 5, illustrated is a method 500 of fabricating a BioFET device using complementary metal oxide semiconductor (CMOS) compatible process(es). FIGS. 6-17 are cross-sectional views of a semiconductor device 600 according to one embodiment, during various fabrication stages of the method 500. It is understood that additional steps can be provided before, during, and after the method 500, and some of the steps described below can be replaced or eliminated, for additional embodiments of the method. It is further understood that additional features can be added in the semiconductor device 600, and some of the features described below can be replaced or eliminated, for additional embodiments of the semiconductor device 600. The method 500 is one embodiment of the method 100, described above with reference to FIG. 1. Further, the method 500, in whole or in part, may be used to fabricate a semiconductor device such as the semiconductor device 200, described above with reference to FIG. 2, a semiconductor device having the layout 300, described above with reference to FIG. 3, and/or the device 400 described above with reference to FIG. 4.

The method 500 begins at block 502 where a device substrate is provided. Block 502 may be substantially similar to block 102 of the method 100, described above with reference to FIG. 1. The device substrate may be a semiconductor substrate (e.g., wafer). The device substrate may be a silicon substrate. Alternatively, the substrate may comprise another elementary semiconductor, such as germanium; a compound semiconductor including silicon carbide, gallium arsenic, gallium phosphide, indium phosphide, indium arsenide, and/or indium antimonide; an alloy semiconductor including SiGe, GaAsP, AlInAs, AlGaAs, GaInAs, GaInP, and/or GaInAsP; or combinations thereof. In an embodiment, the device substrate is a semiconductor on insulator (SOI) substrate. The SOI substrate may include a buried oxide (BOX) layer formed by a process such as separation by implanted oxygen (SIMOX), and/or other suitable processes. The device substrate may include doped regions, such as p-wells and n-wells.

Figure 6:
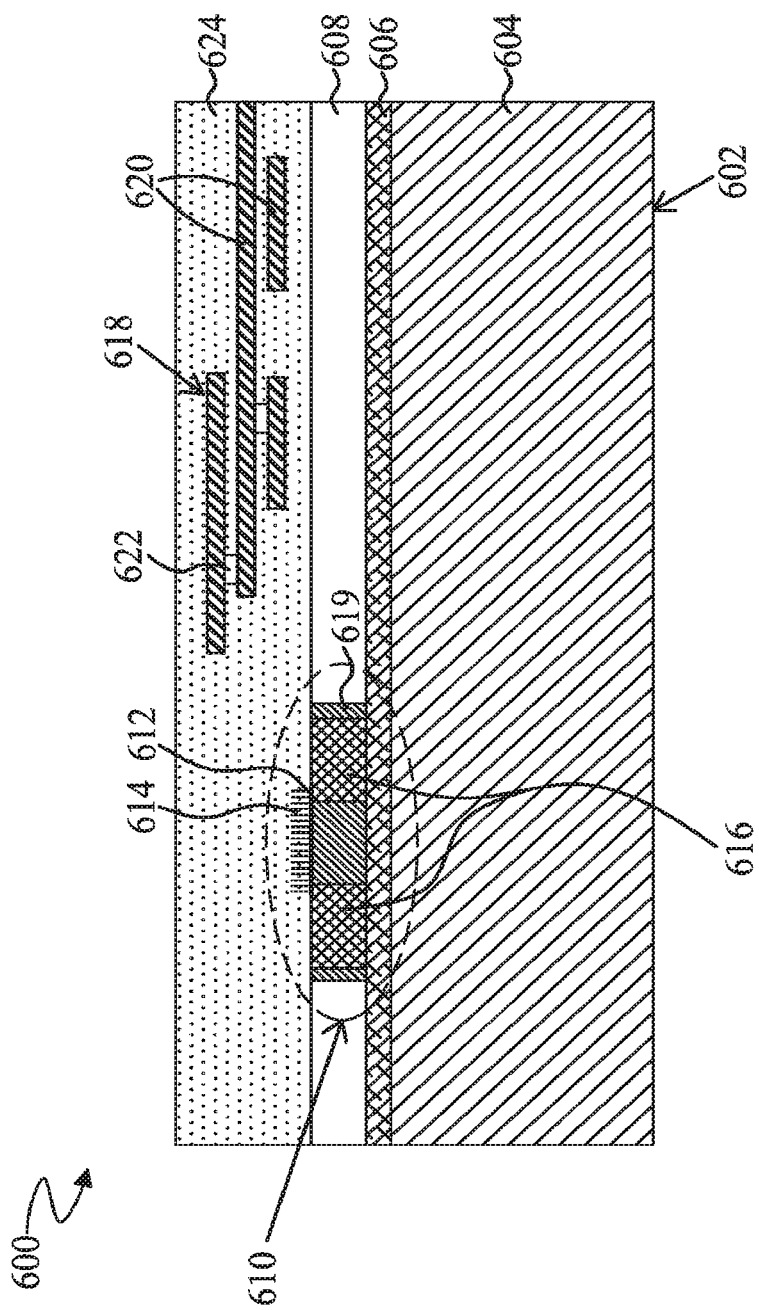
FIGS. 6-17 are cross-sectional views of an embodiment of a BioFET device constructed according to one or more steps of the method of FIG. 5.
Figure 7:
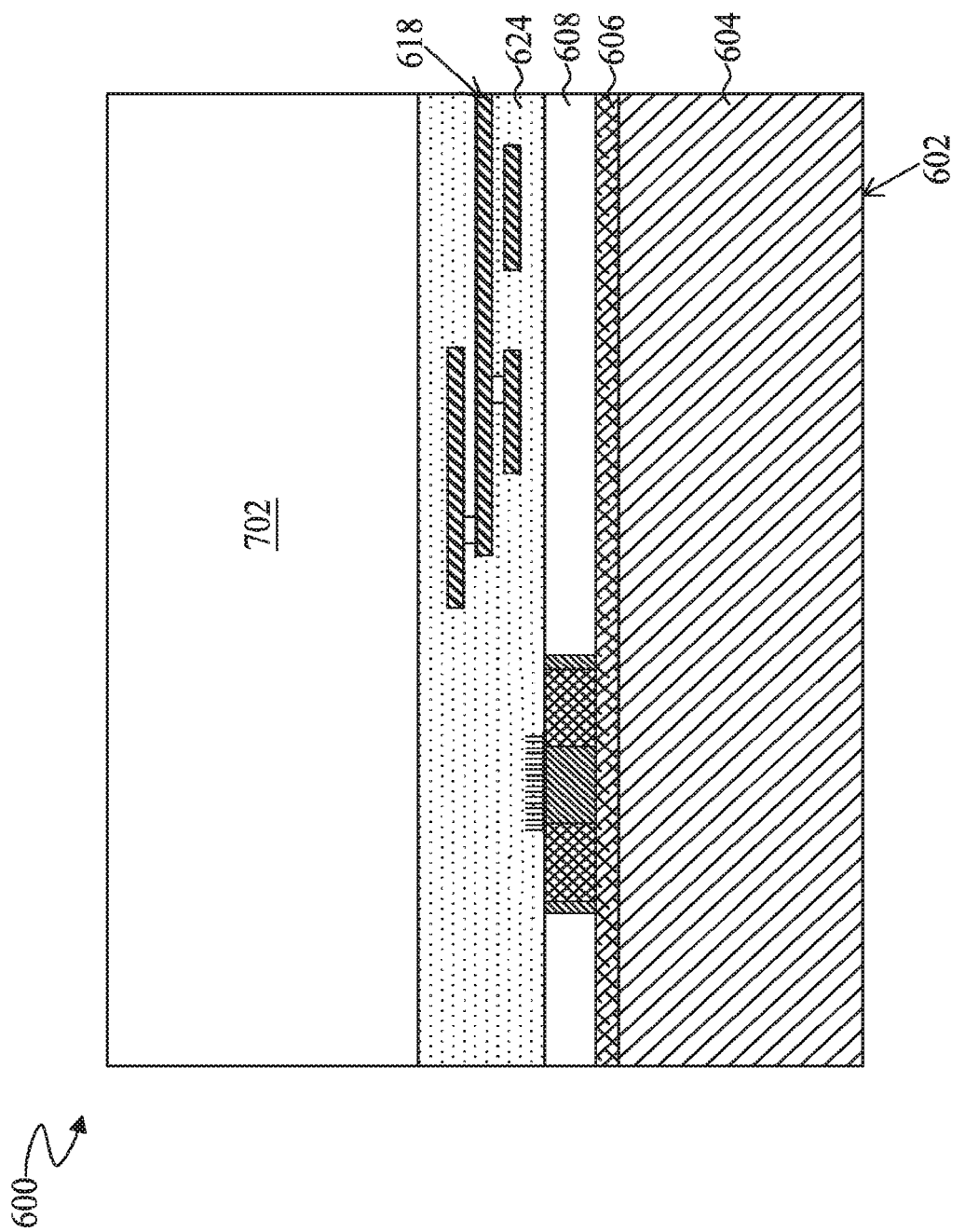

Referring to the example of FIG. 6, a substrate 602 is provided. The substrate 602 is an SOI substrate including a bulk silicon layer 604, an oxide layer 606, and an active layer 608. The oxide layer 606 may be a buried oxide (BOX) layer. In an embodiment, the BOX layer is silicon dioxide ($SiO_2$). The active layer 608 may include silicon. The active layer 608 may be suitably doped with n-type and/or p-type dopants.

The method 500 then proceeds to block 504 where a transistor element is formed on the device substrate. The transistor element may be a field-effect transistor (FET).

Block 504 may be substantially similar to block 104 of the method 100, described above with reference to FIG. 1. The transistor element may include a gate structure, a source region, and a drain region. The gate structure includes a gate electrode and an underlying gate dielectric. However, other configurations are possible. In an embodiment, the gate electrode includes polysilicon. Other exemplary compositions of the gate electrode include suitable metals such as, Cu, W, Ti, Ta, Cr, Pt, Ag, Au; suitable metallic compounds like TiN, TaN, NiSi, CoSi; and/or combinations thereof. The gate electrode material may be deposited by physical vapor deposition (PVD), metal evaporation or sputtering, chemical vapor deposition (CVD), plasma-enhanced chemical vapor deposition (PECVD), atmospheric pressure chemical vapor deposition (APCVD), low-pressure CVD (LPCVD), high density plasma CVD (HDPCVD), or atomic layer CVD (ALCVD). The deposition may be followed by a photolithography process that patterns the deposited material to form one or more gate structures. The gate dielectric may include dielectric material such as, silicon oxide, silicon nitride, silicon oxynitride, dielectric with a high dielectric constant (high k), and/or combinations thereof. Examples of high k materials include hafnium silicate, hafnium oxide, zirconium oxide, aluminum oxide, tantalum pentoxide, hafnium dioxide-alumina ($HfO_2$-$Al_2O_3$) alloy, or combinations thereof. The gate dielectric layer may be formed using conventional processes such as, photolithography, oxidation, deposition processes, including those discussed above, etching, and/or a variety of other processes known in the art. The source and/or drain region may be formed by suitable processes such as using photolithography to define a region for ion implantation, diffusion, and/or other suitable processes.

Referring to the example of FIG. 6, a transistor element 610 is disposed on the substrate 602. The transistor element 610 includes a gate dielectric 612, a gate electrode 614, and source/drain regions 616 disposed in a well 619. The source/drain regions 616 and the well 619 may include opposite-type (e.g., n-type, p-type) dopants. In an embodiment, the gate electrode 614 is a polysilicon gate. In an embodiment, the gate dielectric 612 is a gate oxide layer (e.g., $SiO_2$, $HfO_2$).

The method 500 then proceeds to block 506 where a multi-layer interconnect (MLI) structure is formed on the substrate. The MLI structure may include conductive lines, conductive vias, and/or interposing dielectric layers (e.g., interlayer dielectric (ILD)). The MLI structure may provide physical and electrical connection to the transistor, described above with reference to block 504. The conductive lines may comprise copper, aluminum, tungsten, tantalum, titanium, nickel, cobalt, metal silicide, metal nitride, poly silicon, combinations thereof, and/or other materials possibly including one or more layers or linings. The interposing or inter-layer dielectric layers (e.g., ILD layer(s)) may comprise silicon dioxide, fluorinated silicon glass (FGS), SILK (a product of Dow Chemical of Michigan), BLACK DIAMOND (a product of Applied Materials of Santa Clara, Calif.), and/or other insulating materials. The MLI may be formed by suitable processes typical in CMOS fabrication such as CVD, PVD, ALD, plating, spin-on coating, and/or other processes.

Referring to the example of FIG. 6, an MLI structure 618 is disposed on the substrate 602. The MLI structure 618 includes a plurality of conductive lines 620 connected by conductive vias or plugs 622. In an embodiment, the conductive lines 620 include aluminum and/or copper. In an embodiment, the vias 622 include tungsten. In another embodiment, the vias 622 include copper. A dielectric layer 624 is disposed on the substrate 602 including interposing the conductive features of the MLI structure 618. The dielectric layer 624 may be an ILD layer and/or composed of multiple ILD sub-layers. In an embodiment, the dielectric layer 624 includes silicon oxide. The MLI structure 618 may provide electrical connection to the gate 614 and/or the source/drain 616.

The method 500 then proceeds to block 508 where a carrier substrate is attached (e.g., bonded) to the device substrate. The carrier substrate may be attached to the front side of the device substrate. For example, in an embodiment, the carrier substrate is bonded to the ILD layer. In an embodiment, the carrier substrate is bonded to a passivation layer formed on the MLI and/or ILD layers of the substrate. The carrier substrate may be attached to the device substrate using fusion, diffusion, eutectic, and/or other suitable bonding methods. Exemplary compositions for the carrier substrate include silicon, glass, and quartz. Again however, numerous other compositions are possible and within the scope of the present disclosure. Referring to the example of FIG. 7, a carrier substrate 702 is attached to the device substrate 602. In other embodiments, the carrier substrate 702 may include other functionality such as, interconnect features, wafer bonding sites, defined cavities, and/or other suitable features. The carrier substrate may be removed during subsequent processing (e.g., after thinning).

The method 500 then proceeds to block 510 where the device substrate is thinned. The device substrate may be flipped prior to the thinning. The flipped substrate may provide the source/drain regions overlying the gate structure of the transistor described above with reference to block 504. The device substrate may be thinned using wet etch processes, dry etch processes, plasma etch processes, chemical mechanical polish (CMP) processes, and/or other suitable processes for removing portions of the semiconductor substrate. Example etchants suitable for thinning the substrate include HNA (hydrofluoric, nitric, and acetic acid), tetramethylammonium hydroxide (TMAH), KOH, buffered oxide etch (BOE), and/or other suitable etchants compatible with CMOS process technology.

In an embodiment, the device substrate is thinned such that the bulk silicon layer and the buried insulating layer are removed. The device substrate may be thinned in a plurality of process steps, for example, first removing the bulk silicon layer of an SOI wafer followed by removal of a buried insulating layer of the SOI wafer. In an embodiment, a first thinning process includes removal of the bulk silicon using, for example, CMP, HNA, and/or TMAH etching, which stops at the buried oxide layer. The first thinning process may be followed by a second thinning process, such as BOE wet etch, which removes the buried oxide and stops at the silicon of the active layer. The thinning process may expose an active region of the substrate. In an embodiment, a channel region (e.g., active region interposing the source/drain regions and underlying the gate structure) is exposed. The substrate may have a thickness of approximately 500 Angstroms (A) to 1500 A after the thinning process. For example, in one embodiment the active region of an SOI substrate has a thickness of between of approximately 500 A and 1500 A.

In an embodiment, the device substrate is thinned such that the bulk silicon layer is removed, and the buried insulating layer remains on the substrate. The removal of the bulk silicon may be performed using, for example, CMP, HNA, and/or TMAH etching, which stops at the buried insulating layer. The substrate may have a thickness of approximately 500 Angstroms (A) to 1500 A after the thinning process. For example, in one embodiment the active region of an SOI substrate has a thickness of between of approximately 500 A and 1500 A. The buried insulating layer (now providing the surface of the substrate) may perform as an isolation layer such as described below with reference to block 514. Thus, an additional isolation layer does not require deposition.

Figure 8:
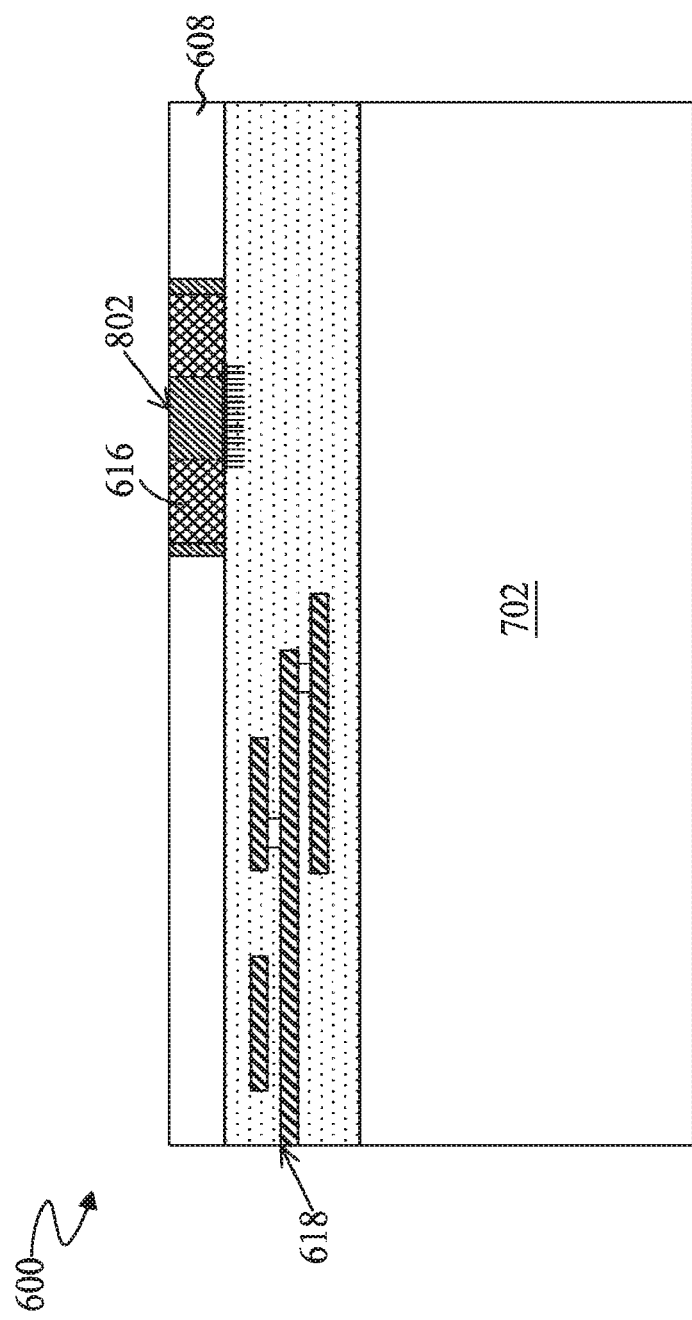
Figure 9:
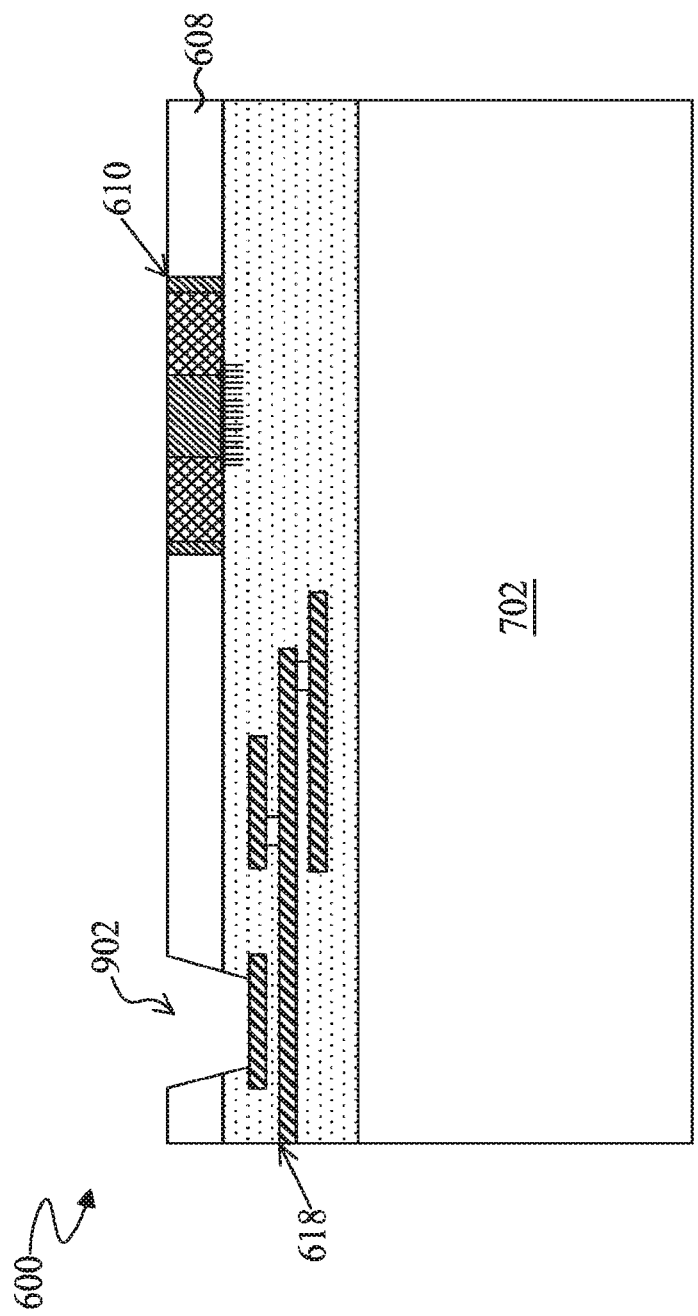
Figure 10:
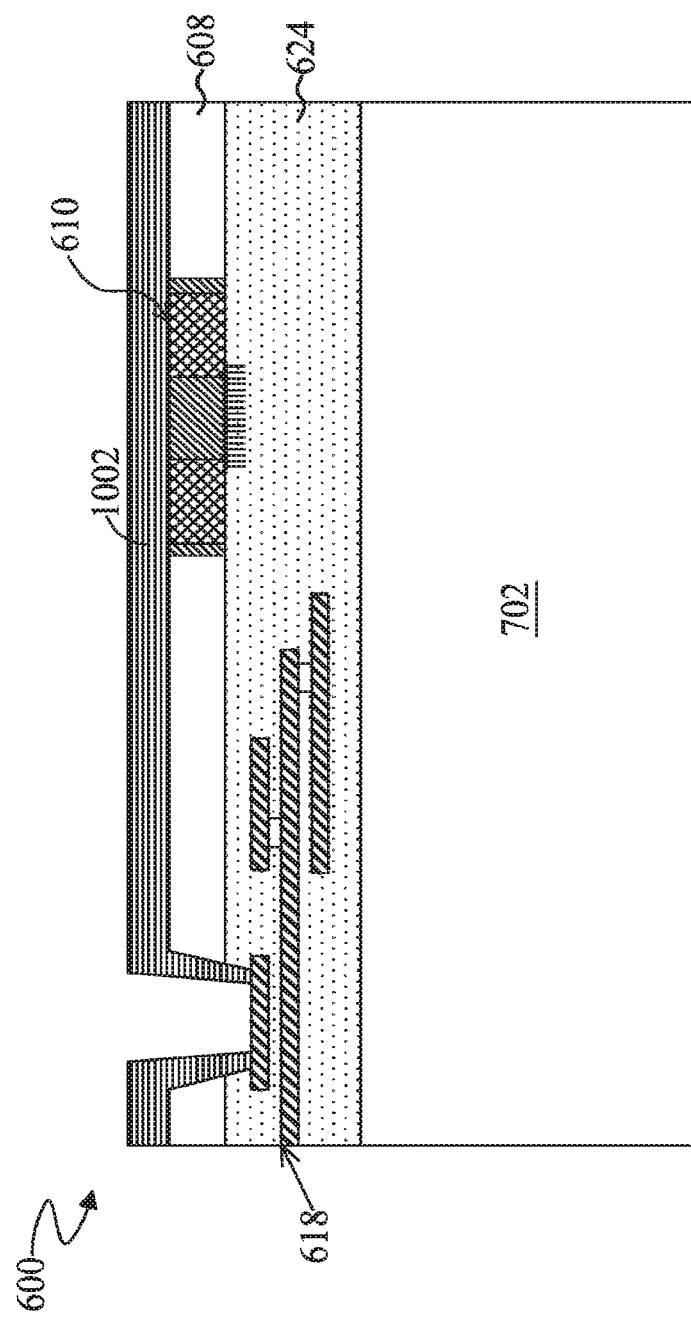
Figure 11:
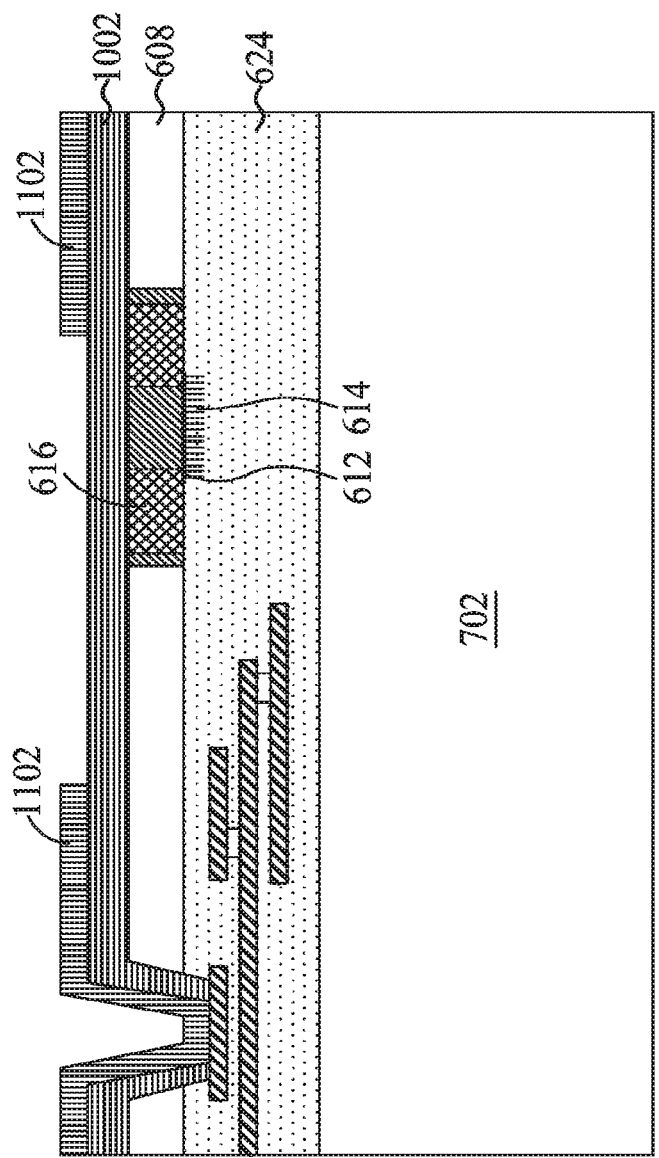

Referring to the example of FIG. 8, the substrate 602 has been thinned removing the bulk silicon layer 604 and the buried oxide layer 606, described above with reference to FIG. 6. The thinning process may include using at least one of the buried oxide layer 606 or the active layer 608 as an etch stop layer. The thinning exposes a channel region 802 (formed in the active layer 608) of the transistor element 610.

In an embodiment, the bulk silicon layer 604 may be removed and the buried oxide layer 606 may remain and function, for example, in addition to or in lieu of an insulating layer 1002, described below.

The method 500 then proceeds to block 512 where a trench is formed on the substrate to expose and provide contact to one or more of the conductive traces of the MLI structure. The trench may be formed by photolithography processes to pattern the trench opening followed by suitable wet, dry or plasma etching processes. In an embodiment, the trench exposes a portion of a metal one (metal 1) layer of the MLI (e.g., the first metal layer formed in the MLI structure after the gate structure is formed). Referring to the example of FIG. 9, a trench 902 is etched in the substrate 602, specifically through the active layer 608, to expose a landing region on a conductive line 620 of the MLI structure 618. Alternatively, the trench may be etched through the isolation region (e.g., oxide).

The method 500 then proceeds to block 514 where an isolation layer is formed on the substrate. The isolation layer may include a dielectric material such as an oxide or nitride. In an embodiment, the isolation layer is silicon oxide. Referring the example of FIG. 10, an isolation layer 1002 is disposed on the active layer 608. In an embodiment, the isolation layer 1002 is silicon dioxide. As discussed above, in an embodiment, an isolation layer is not formed as the insulating layer of the SOI substrate remains on the substrate and functions to replace the need (in whole or in part) for a separate isolation layer.

The method 500 then proceeds to block 516 where an interconnect layer is formed on the isolation layer of described above with reference to block 514. The interconnect layer may provide a connection (e.g., I/O connection) to the MLI structure, described above with reference to block 506. The interconnect layer may provide a connection (e.g., I/O connection) to the transistor 610. The interconnect layer may include a conductive material such as, copper, aluminum, combinations thereof, and/or other suitable conductive material. The interconnect layer may provide functions as a re-distribution layer (RDL). Referring to the example of FIG. 11, an interconnect layer 1102 is disposed on the insulating layer 1002. The interconnect layer 1102 may provide a signal input/output to the transistor 610. In an embodiment, the interconnect layer 1102 includes an aluminum copper alloy.

The method 500 then proceeds to block 518 where a passivation layer is formed on the device substrate. The passivation layer may cover portions of the interconnect layer described above with reference to block 516. The passivation layer may include openings where a bond (e.g., I/O) may be formed. In an embodiment the passivation layer includes silicon dioxide, however, other compositions are possible. The passivation layer may be suitable to provide protection of the device, e.g., the interconnect layer, including from moisture. Referring to the example of FIG. 12, a passivation layer 1202 is formed on the substrate including on the interconnect layer 1102. The passivation layer 1202 includes an opening 1204 where a bond (e.g., wire bond, bump) may provide connection (e.g., I/O connection) to the device 600. In other words, the opening 1204 may expose a conductive I/O pad.

Figure 13:
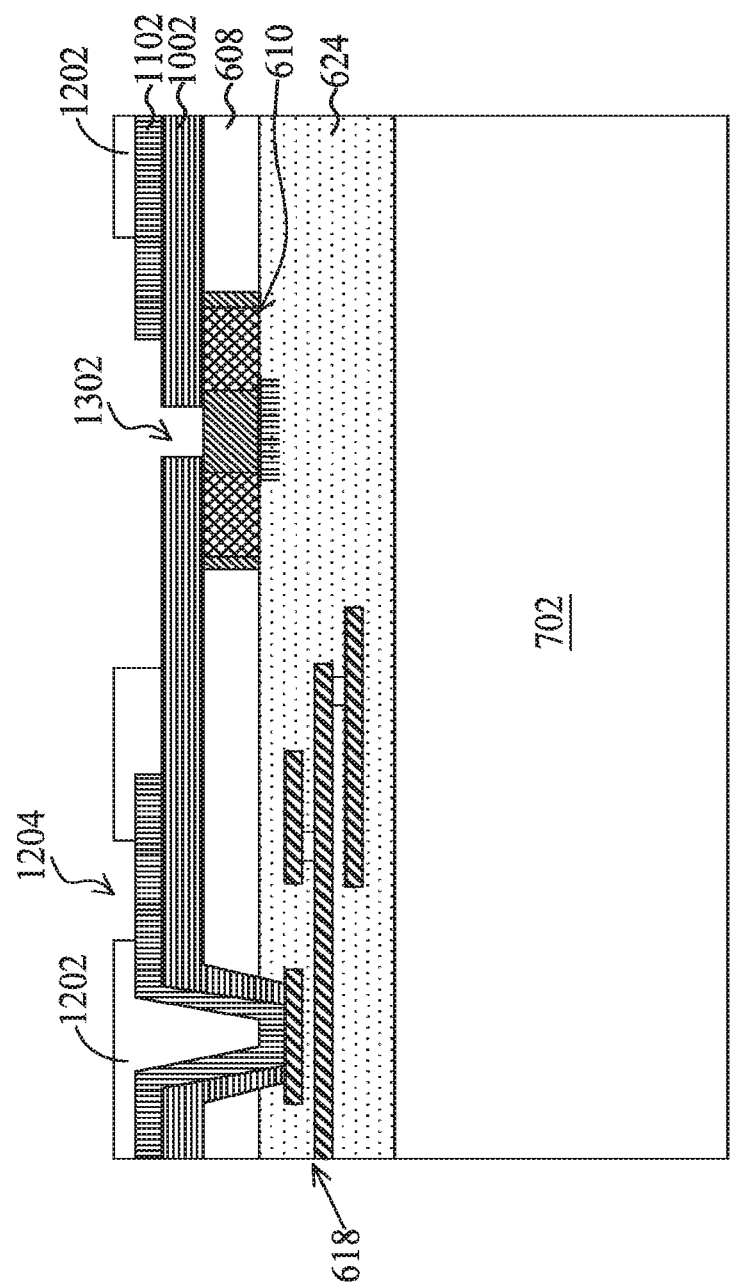
Figure 14:
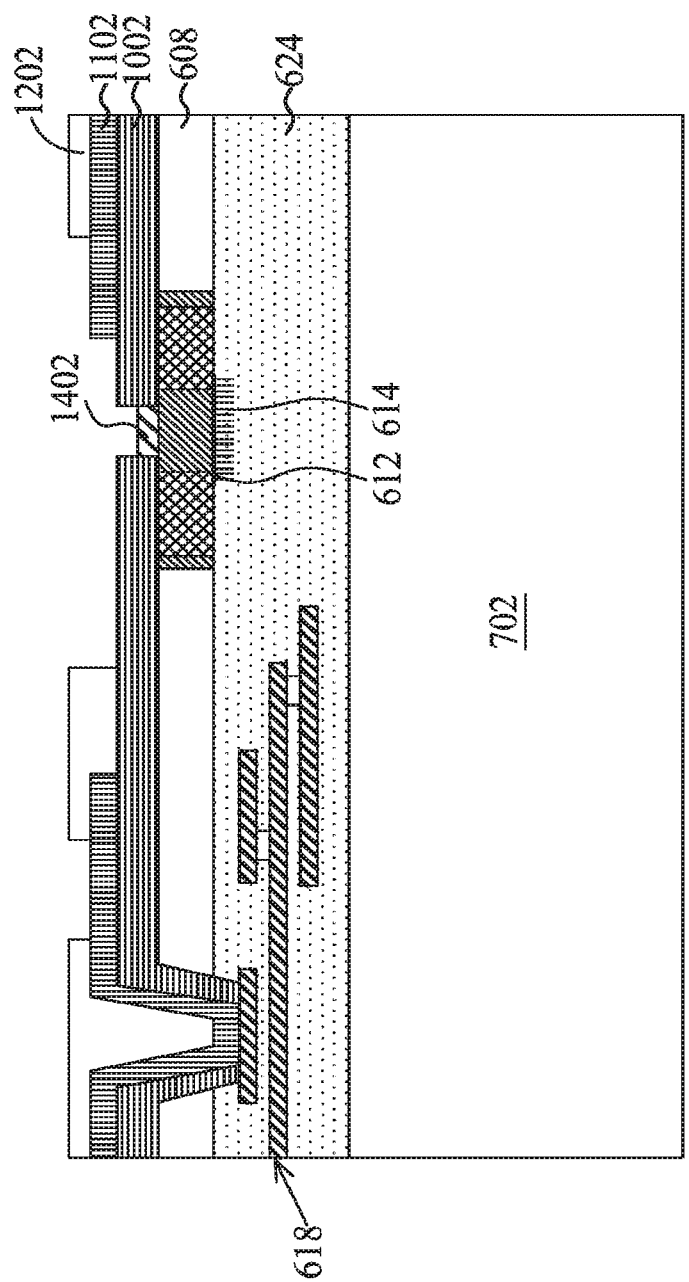
Figure 15:
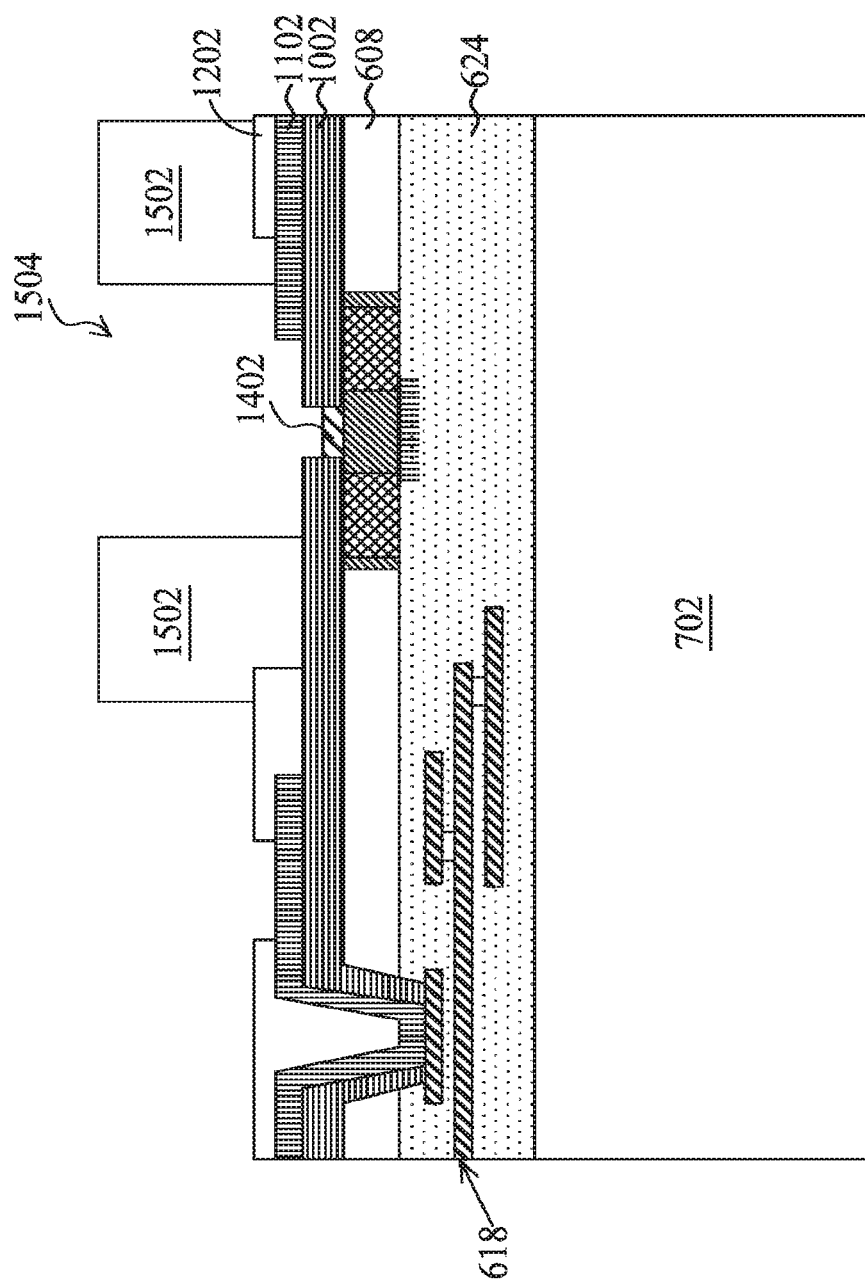

The method 500 then proceeds to block 520 where an opening is formed on the backside of the substrate. The opening may be formed such that a portion of the active region of the substrate underlying the transistor structure (e.g., channel region) is exposed. The opening may be substantially aligned with the gate structure of the transistor. The opening may be formed by suitable photolithography processes followed by an etching process such as a dry etch, wet etch, plasma etch, and/or combinations thereof. In an embodiment, the opening is formed in the isolation layer, described above with reference to block 514. In an embodiment, the opening is formed in the buried insulator layer (of the SOI substrate). Referring to FIG. 13, an opening 1302 is provided. The opening 1302 exposes a portion of the active layer 608. In particular, a channel region 802 of the active layer 608 may be exposed.

The method 500 then proceeds to block 522 where an interface layer is formed on the substrate in the exposed active region provided by the opening. Block 522 may be substantially similar to block 108 of the method 100, described above with reference to FIG. 1. The interface layer may include a material for any specified bio-molecule binding. In an embodiment, the interface layer includes a high-k dielectric material such as, $HfO_2$. In an embodiment, the interface layer includes a metal layer such as Pt, Au, Al, W, Cu, and/or other suitable metal. Other exemplary interface materials include high-k dielectric films, metals, metal oxides, dielectrics, and/or other suitable materials. As a further example, exemplary interface materials include $HfO_2$, $Ta_2O_5$, Pt, Au, W, Ti, Al, Cu, oxides of such metals, $SiO_2$, $Si_3N_4$, $Al_2O_3$, $TiO_2$, TiN, SnO, $SnO_2$; and/or other suitable materials. The interface layer may include a plurality of layers of material. The interface layer may be formed using suitable CMOS processes including CVD, PVD, ALD, and/or other suitable deposition methods. Referring to the example of FIG. 14, an interface layer 1402 is disposed on the active layer 608. The interface layer 1402 can be patterned to be aligned with the gate structure (e.g., is disposed and patterned to remain only in the opening 1302.)

The method 500 then proceeds to block 524 where a fluidic channel is disposed on the device substrate. The fluidic channel may define a region overlying the interface layer such that a solution may be maintained on the interface layer. The fluidic channel may be formed by soft lithography utilizing polydimethylsiloxane (PDMS), wafer bonding methods, and/or other suitable methods. The fluidic channel may be substantially similar to the fluidic channel 406, described above with reference to FIG. 4. Referring to the example of FIG. 15, a fluidic channel 1502 is disposed on the substrate. The fluidic channel 1502 provides a cavity 1504 overlying the interface layer 1402. A solution may be disposed in the cavity 1504, as described in further detail below.

The method 500 then proceeds to block 526 where a receptor is disposed on the interface layer. The receptor may include enzymes, antibodies, ligands, receptors, peptides, nucleotides, cells of organs, organisms and pieces of tissue.

Figure 16:
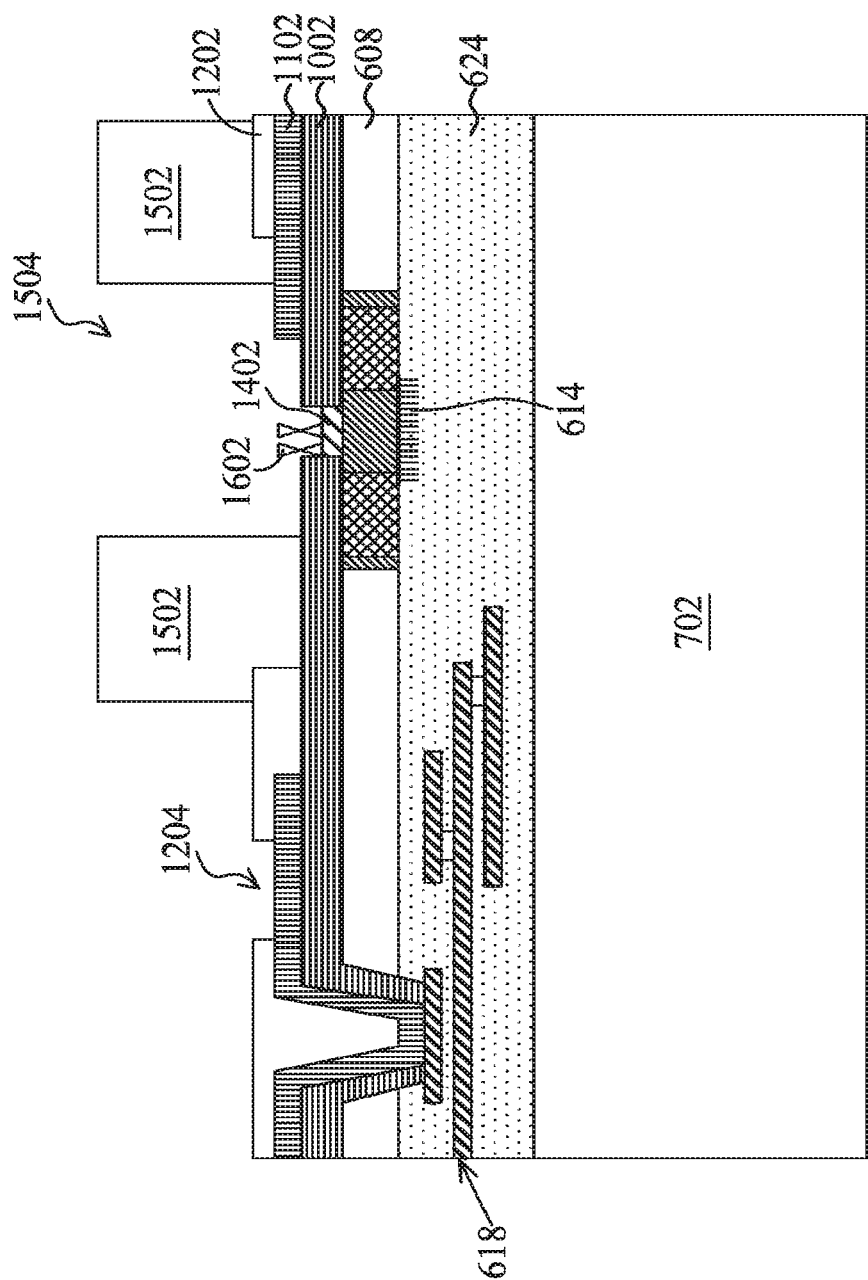

Referring to the example of FIG. 16, a plurality of receptors 1602 is disposed on the interface layer 1042.

The method 500 then proceeds to block 528 where a solution that contains target molecules is provided in the fluidic channel.

Figure 17:
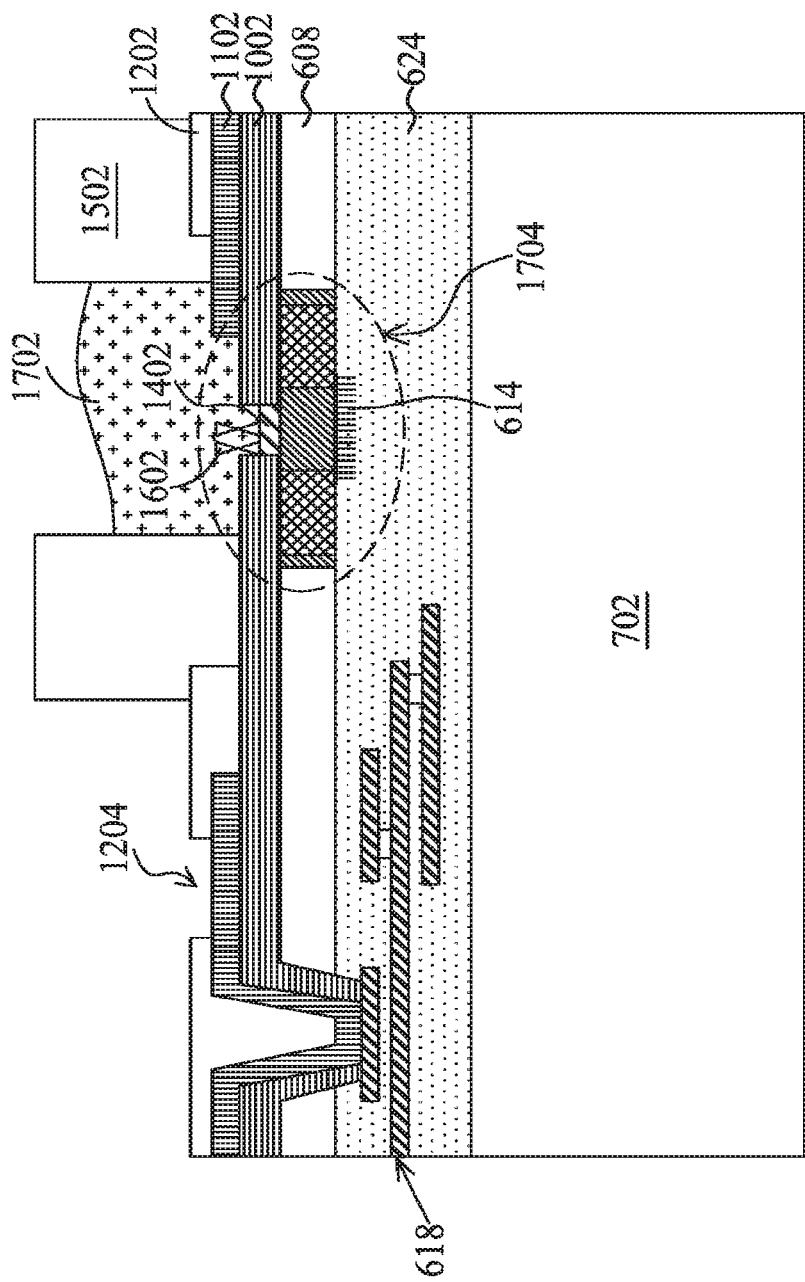

Referring to the example of FIG. 17, a solution 1702 is disposed in the fluidic channel 1502. The solution 1702 contacts the receptors 1602.

In embodiments of the method 500, blocks 524, 526, and/or 528 may be omitted, performed by a different entity, and/or performed outside of a CMOS process.

Thus, the FET 610 is modified to provide the BioFET 1704. The BioFET 1704 allows receptor 1602 to control the conductance of the BioFET 1704, while the gate structure 614 (e.g., polysilicon) provides a back gate. The gate structure 614 provides a back gate that can control the channel electron distribution without a bulk substrate effect. If the receptors 1602 attach to a molecule provided on an interface layer 1402, the resistance of the field-effect transistor channel 802 in the active layer 608 between the source/drain 616 is altered. Therefore, the BioFET 1704 may be used to detect one or more specific molecules, including biomolecules or bio-entities, in the environment around and/or in the opening 1302. The BioFET 1704 may be arranged in an array type pattern such as described above with reference to FIGS. 3 and/or 4. The interconnect 1102 may provide a bias to the BioFET 1704 including, for example, to the front gate or receptor 1602/interface layer 1402 gate.

Referring now to FIG. 18, illustrated is a method 1800 of fabricating a BioFET device using complementary metal oxide semiconductor (CMOS) process(es). FIGS. 19-26 are cross-sectional views of a semiconductor device 1900 according to one embodiment, during various fabrication stages of the method 1800. It is understood that additional steps can be provided before, during, and after the method 1800, and some of the steps described below can be replaced or eliminated, for additional embodiments of the method. It is further understood that additional features can be added in the semiconductor device 1900, and some of the features described below can be replaced or eliminated, for additional embodiments of the semiconductor device 1900. The method 1800 is one embodiment of the method 100, described above with reference to FIG. 1. Further, the method 1900 may be used to fabricate a semiconductor device such as the semiconductor device 200, described above with reference to FIG. 2, a semiconductor device having the layout 300, described above with reference to FIG. 3, and/or the device 400 described above with reference to FIG. 4.

The method 1800 begins at block 1802 where a device substrate is provided. Block 1802 may be substantially similar to block 102 of the method 100, described above with reference to FIG. 1 and/or block 502, described above with reference to the method 500 of FIG. 5. Referring to the example of FIG. 19, a substrate 1902 is provided. The substrate 1902 is an SOI substrate including a bulk silicon layer 1904, an oxide layer 1906, and an active layer 1908. The oxide layer 1906 may be a buried oxide (BOX) layer. In an embodiment, the BOX layer is silicon dioxide ($SiO_2$). The active layer 1908 may include silicon that is suitably doped in various regions.

The method 1800 then proceeds to block 1804 where a transistor element is formed on the device substrate. The transistor element may be a field-effect transistor (FET). Block 1804 may be substantially similar to block 104 of the method 100, described above with reference to FIG. 1, and/or may be substantially similar to block 504 of the method 500, described above with reference to FIG. 5. Referring to the example of FIG. 19, a transistor element 1910 is disposed on the substrate 1902. The transistor element 1910 includes a gate dielectric 1912, a gate electrode 1914, and source/drain regions 1916 disposed in a well 1919. The source/drain regions 1916 and the well 1919 may be regions that include opposite-type (e.g., n-type, p-type) dopants. In an embodiment, the gate electrode 1914 is a polysilicon gate. Other exemplary gate electrodes 1914 include metal. In an embodiment, the gate dielectric 1912 is a gate oxide layer. Other exemplary gate dielectric 912 compositions include high-k dielectrics, nitrides, oxynitrides, and/or other suitable dielectric materials.

The method 1800 then proceeds to block 1806 where an MLI structure is formed on the substrate. The MLI structure may include conductive lines, conductive vias, and/or interposing dielectric layers (e.g., ILD layer(s)). The MLI structure may provide physical and electrical connection to the transistor, described with reference to block 1804. Block 1806 may be substantially similar to block 506 of the method 500, described above with reference to FIG. 5.

Figure 19:
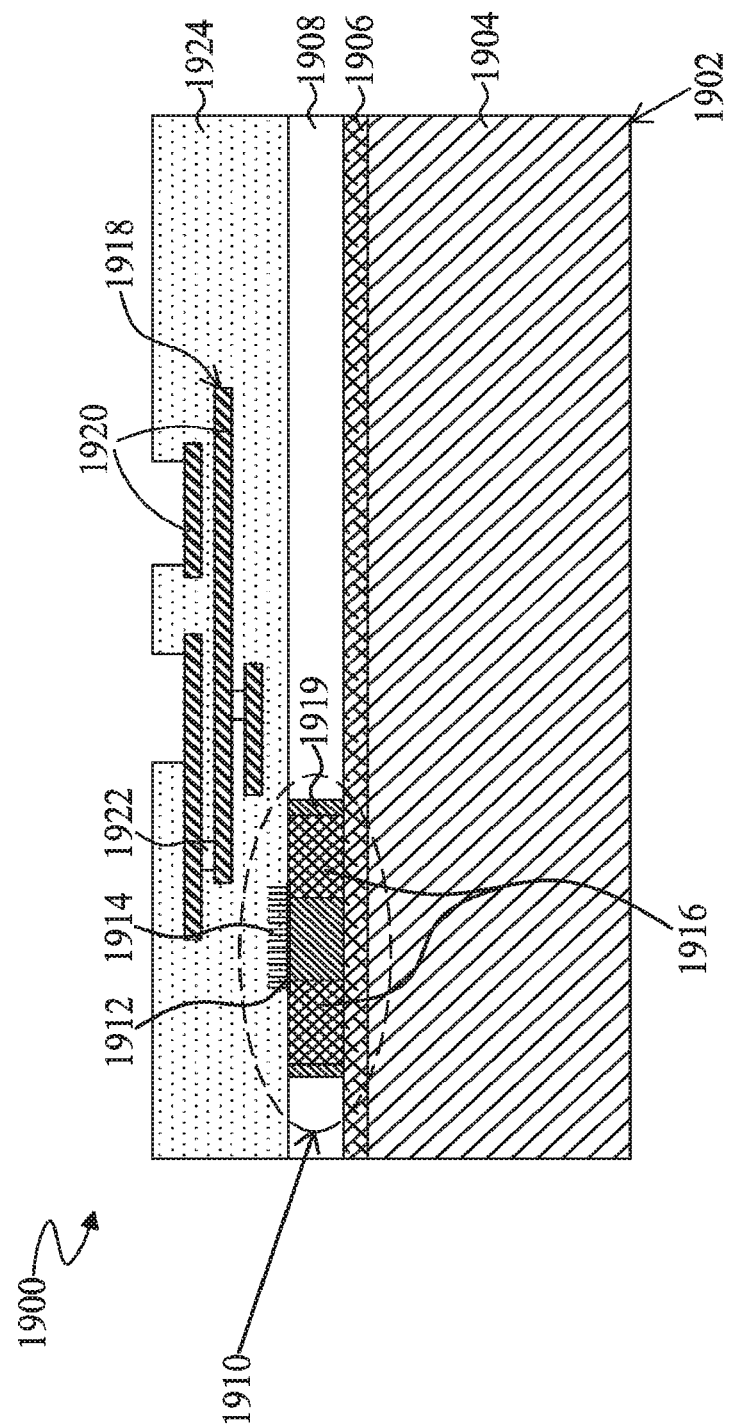
FIGS. 19-26 are cross-sectional views of an embodiment of a BioFET device constructed according to one or more steps of the method of FIG. 18.

Referring to the example of FIG. 19, an MLI structure 1918 is disposed on the substrate 1902. The MLI structure 1918 includes a plurality of conductive lines 1920 connected by conductive vias or plugs 1922. In an embodiment, the conductive lines 1920 include aluminum and/or copper. In an embodiment, the vias 1922 include tungsten. However, other conductive compositions for the conductive lines 1920 and/or vias 1922 are possible. A dielectric layer 1924 is disposed on the substrate 1902 including interposing the conductive features of the MLI structure 1918. The dielectric layer 1924 may be an ILD layer or composed of multiple ILD sub-layers. In an embodiment, the dielectric layer 1924 includes silicon oxide. Again however, other embodiments are possible. The MLI structure 1918 may provide electrical connection to the transistor 1910 including gate 1914 and/or the source/drain 1916.

The method 1800 then proceeds to block 1808 where a carrier (or handling) substrate is attached (e.g., bonded) to the device substrate. The carrier substrate may be attached to the front side of the device substrate. For example, in an embodiment, the carrier substrate is bonded to the ILD layer. In an embodiment, the carrier substrate is bonded to a passivation layer disposed on the MLI and/or ILD layer(s). The carrier substrate may be attached to the device substrate using fusion, diffusion, eutectic, and/or other suitable bonding methods. Exemplary compositions for the carrier substrate include silicon, glass, and quartz. However, numerous other compositions are possible and within the scope of the present disclosure. In an embodiment, one or more conductive layers are provided on the carrier substrate. The conductive layers may be connected (e.g., physically and/or electrically) to one or more devices on the substrate 1902. In an embodiment, the carrier substrate includes a bond pad.

Figure 20:
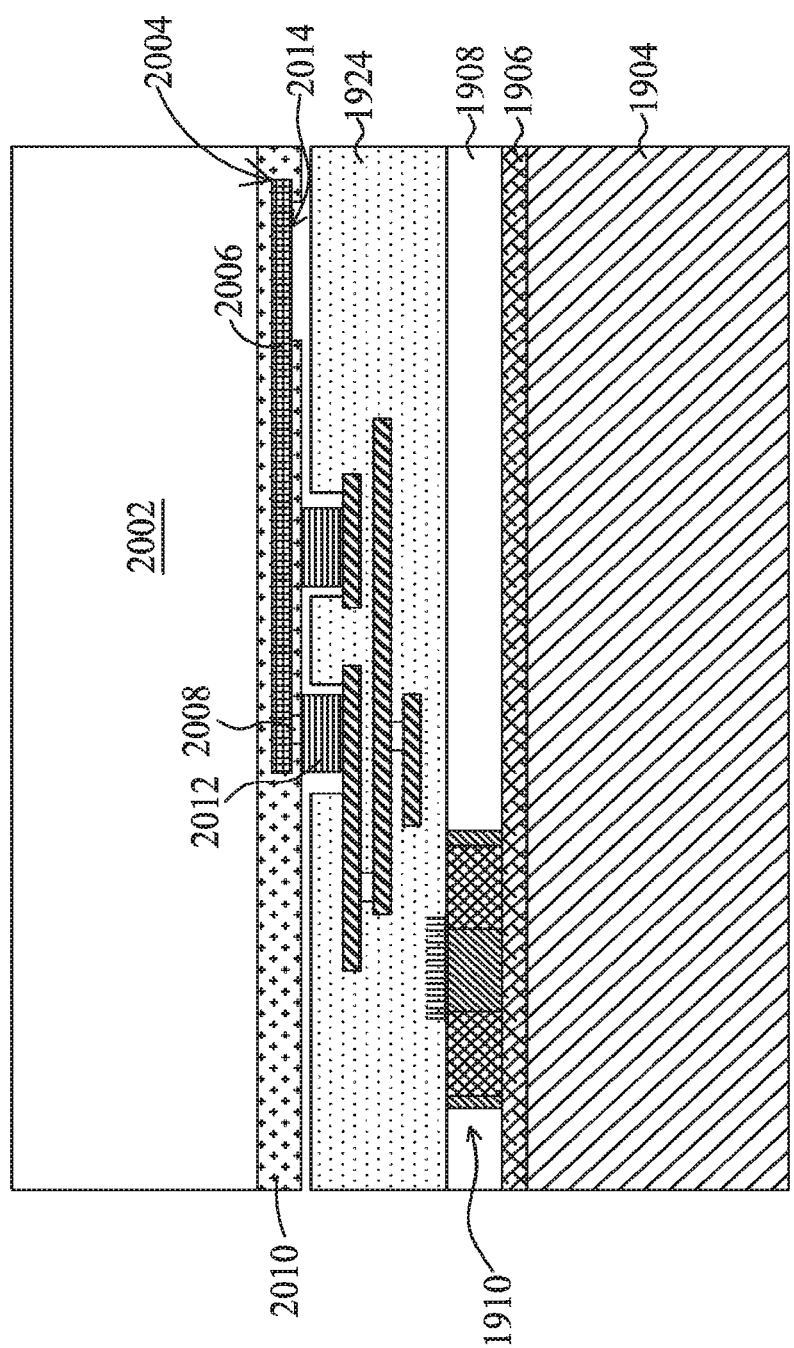
Figure 21:
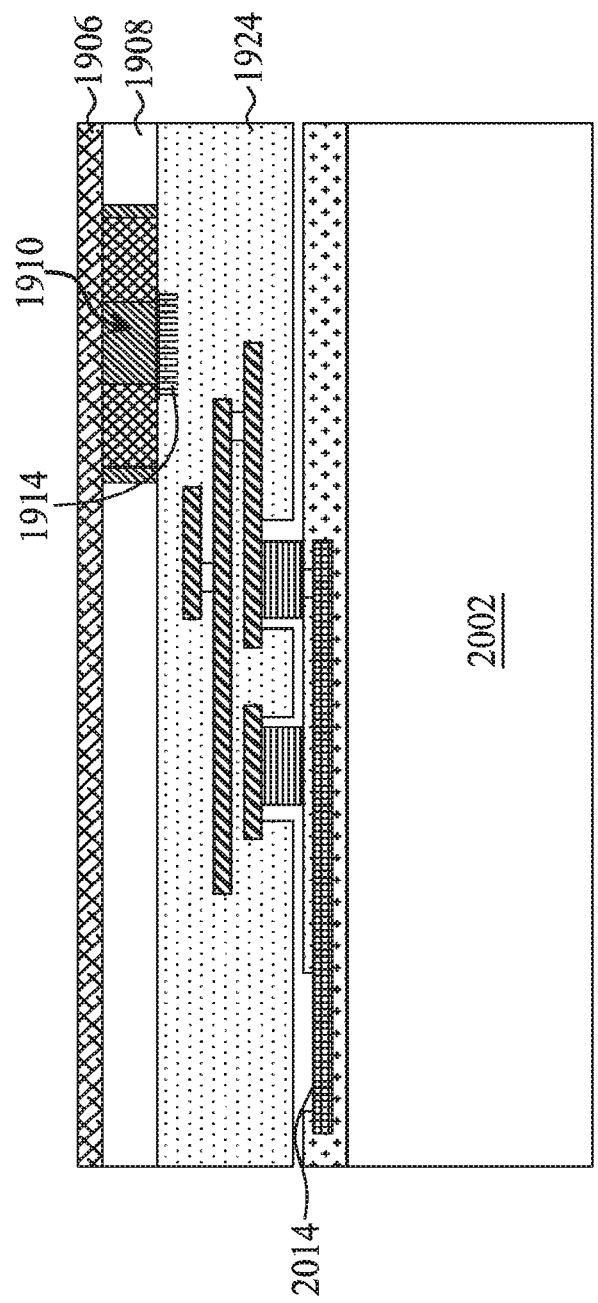
Figure 22:
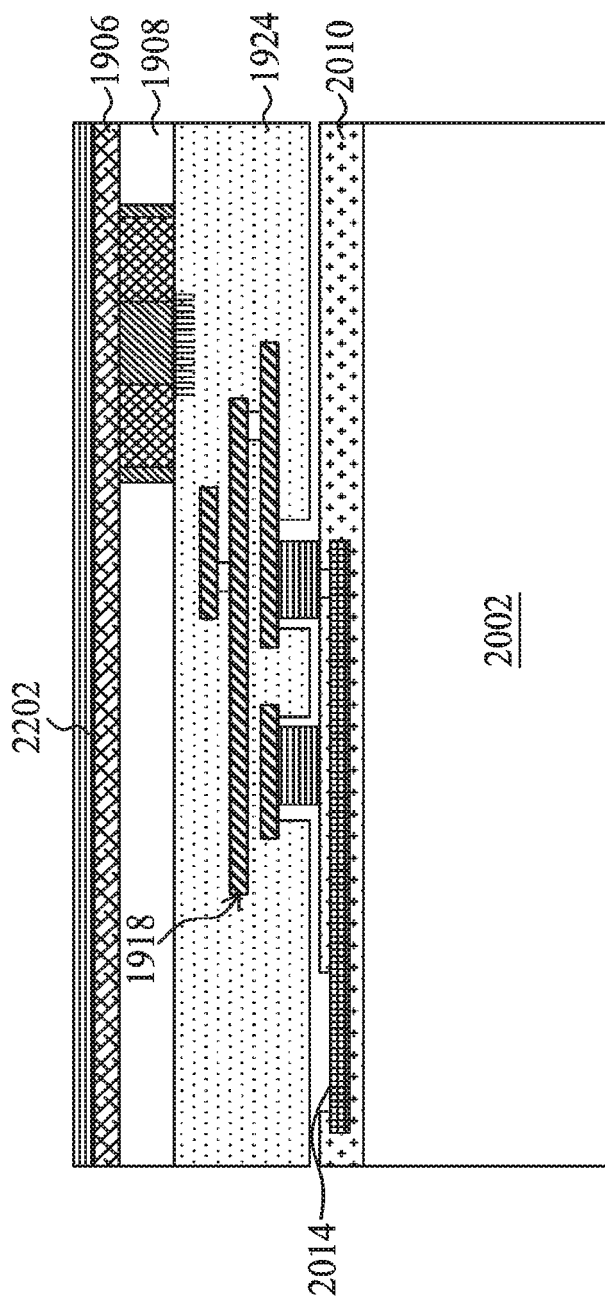
Figure 23:
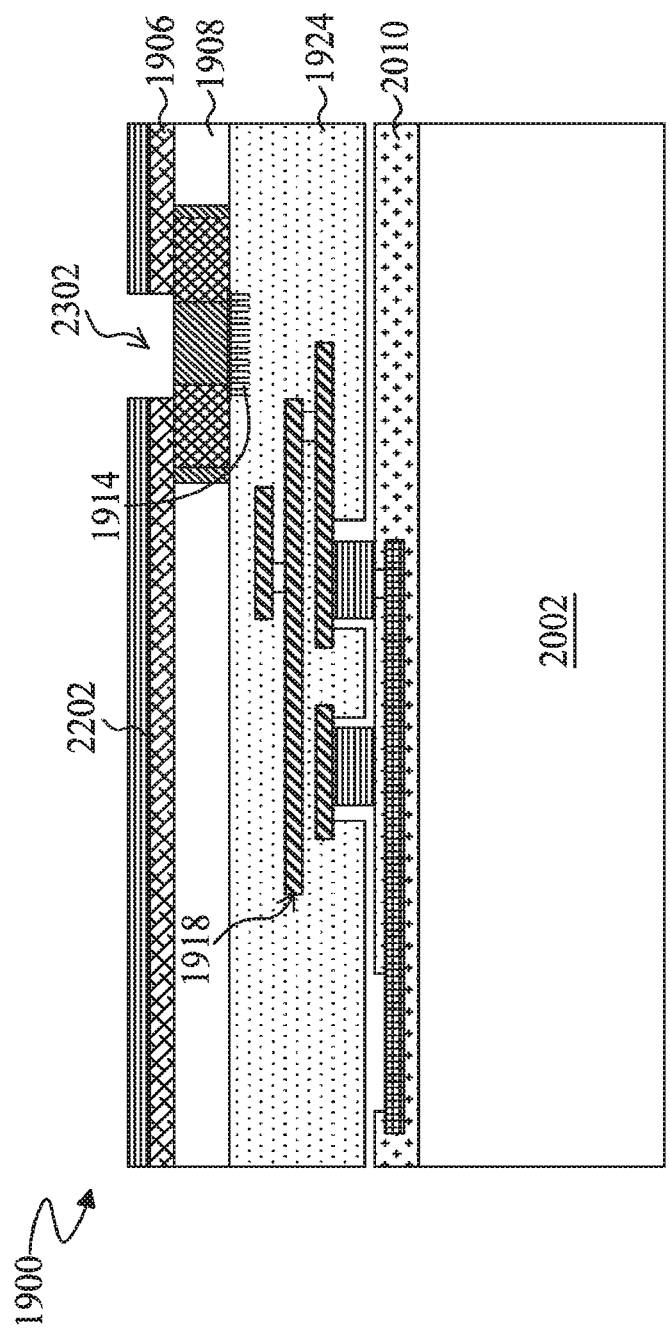
Figure 24:
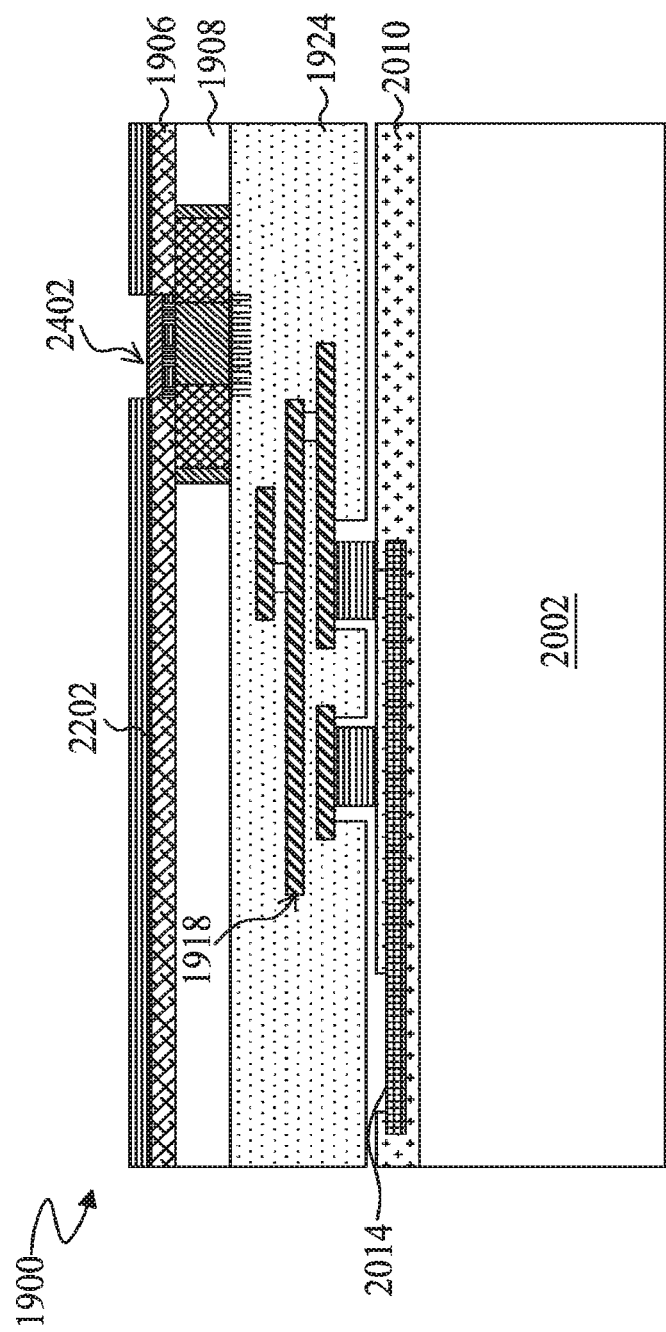
Figure 25:
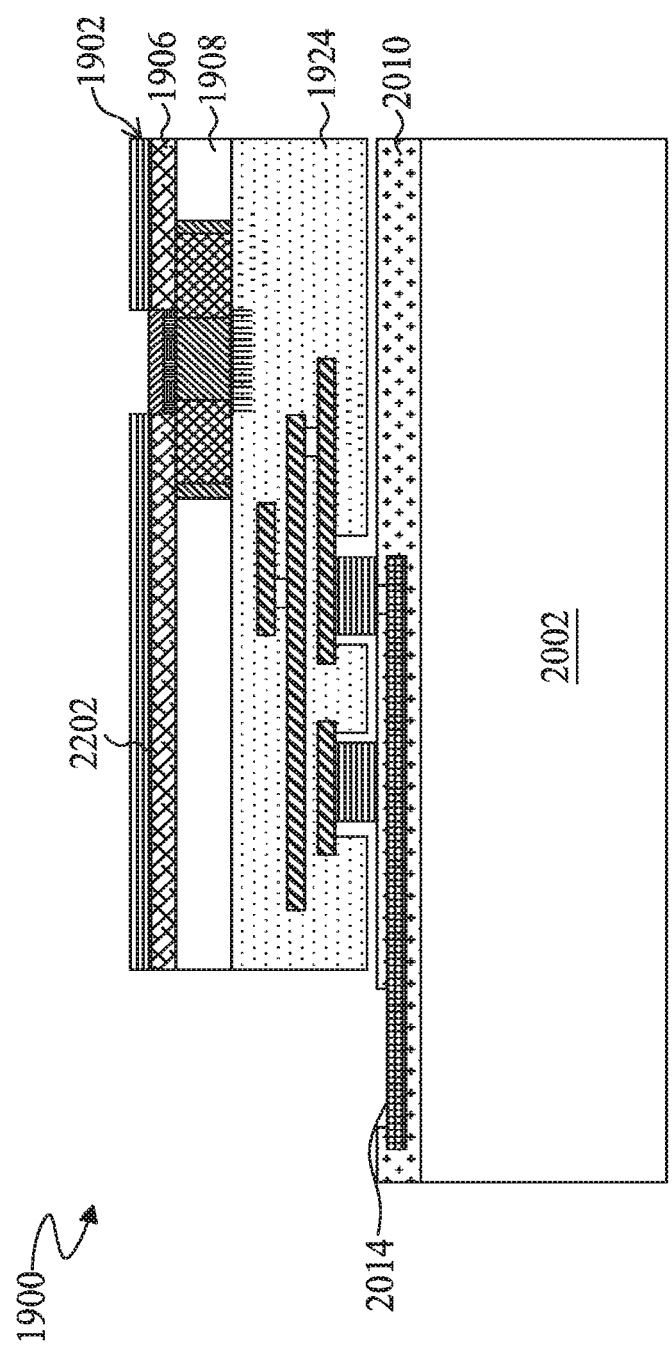

Referring to the example of FIG. 20, a carrier substrate 2002 is attached to the device substrate 1902. In an embodiment, the carrier substrate 2002 is silicon. The carrier substrate 2002 includes an interconnect scheme 2004 including a conductive trace 2006 and via 2008, however other interconnect schemes may be possible including those providing different routings, those including a plurality of layers of conductive traces, and/or other suitable interconnect methods. The interconnect scheme 2004 is disposed in an insulating layer 2010. In an embodiment, the insulating layer is silicon oxide.

The interconnect scheme 2004 includes a bonding element 2012 which is connected (e.g., physically and/or electrically) to the device substrate 1902, for example, to the MLI structure 1918. The bonding element 2012 may include a eutectic bond or metal-to-metal diffusion bond. In an embodiment, the bonding element 2012 is a eutectic bond between Ge—AlCu alloy. Numerous other eutectic bonding compositions are possible. The interconnect scheme 2004 further includes an I/O pad 2014. The I/O pad 2014 may be suitable for connection to a wire bond, bump, ball, and/or other bonding means to provide connection from the device 1900 to other devices and/or instrumentation.

The method 1800 then proceeds to block 1810 where the device substrate is thinned. Block 1810 may be substantially similar to block 510 of the method 500, described above with reference to FIG. 5. The device substrate may be thinned using wet etch processes, dry etch processes, plasma etch processes, chemical mechanical polish (CMP) processes, and/or other suitable processes for removing portions of the semiconductor substrate. Example etchants include HNA, TMAH, KOH, BOE, and/or other suitable etchants compatible with CMOS process technology. In an embodiment, an SOI substrate is thinned such that a buried insulator (e.g., oxide BOX) remains on the substrate, while the bulk silicon is removed. Referring to the example of FIG. 21, the substrate 1902 has been thinned removing the bulk silicon layer 1904, described above with reference to FIG. 19. The thinning process may include using the buried oxide layer 1906 as an etch stop layer. In other embodiments, the buried oxide layer 1906 may be removed.

The method 1800 then proceeds to block 1812 where an isolation layer is formed on the substrate. The isolation layer may include a dielectric material such as an oxide or nitride. In an embodiment, the isolation layer is silicon nitride. The isolation material may provide a protective barrier (e.g., moisture barrier). Referring the example of FIG. 22, an isolation layer 2202 is disposed on the buried oxide layer 1906 and the active layer 1908. In an embodiment, the isolation layer 2202 is silicon nitride.

The method 1800 then proceeds to block 1814 where an opening is formed on the backside of the substrate. The opening may be formed such that a portion of the active region of the substrate underlying the transistor structure (e.g., channel region) is exposed. The opening may be substantially aligned with the gate structure of the transistor. The opening may be formed by suitable photolithography processes followed by an etching process such as a dry etch, plasma etch, wet etch, and/or combinations thereof. In an embodiment, the opening is formed in the isolation layer, described above with reference to block 1812 and the buried oxide layer of an SOI substrate. Referring to the example of FIG. 23, an opening 2302 is provided. The opening 2302 exposes a portion of the active region 1908. In particular, a channel region of the active region 1908 may be exposed.

The method 1800 then proceeds to block 1816 where an interface layer is formed on the substrate in the opening, for example, on the exposed active region. Block 1816 may be substantially similar to block 108 of the method 100, described above with reference to FIG. 1 and/or may be substantially similar to the block 522 of the method 500, described above with reference to FIG. 5. Referring to the example of FIG. 24, an interface layer 2402 is disposed on the active region 1908. The interface layer 2402 is aligned with the gate structure (e.g., is disposed above the gate structure 1914.) The interface layer 2402 includes a first layer and a second layer. In an embodiment, the first layer is a high-k dielectric material (e.g., $HfO_2$). In an embodiment, the second layer is a metal (e.g., Au).

The method 1800 then proceeds to block 1818 where an I/O bond pad provided on the carrier substrate is exposed. In an embodiment, the device substrate is diced and/or etched such that a conductive pad is exposed on the carrier substrate. The conductive pad or bond pad may provide connection (e.g., I/O connection) to the device 1900. Numerous connection methods may be employed to provide a connection to the device via the bond pad including wire bonding, bumping, conductive ball connections, and/or other suitable I/O connections. Referring to the example of FIG. 25, the device substrate 1902 is diced and/or etched to remove a portion of the substrate 1902 overlying the carrier substrate 2002 including the I/O pad 2014.

The method 1800 then proceeds to block 1820 where a fluidic channel is disposed on the device substrate. The fluidic channel may define a region overlying the interface layer such that a solution may be maintained on the interface layer. The fluidic channel may be formed by PDMS methods, wafer bonding methods, and/or other suitable methods. The fluidic channel may be substantially similar to the fluidic channel 406, described above with reference to FIG. 4. Block 1820 may be substantially similar to block 524 of the method 500, described above with reference to FIG. 5. In an embodiment, block 1820 is provided prior to block 1818 of the method 1800. Referring to the example of FIG. 26, a fluidic channel 2602 is disposed on the substrate. The fluidic channel 2602 provides a cavity 2604 overlying the interface layer 2402. A solution may be disposed in the cavity 2604.

The method 1800 then proceeds to block 1822 where a receptor is disposed on the interface layer. Block 1822 may be substantially similar to block 526 of the method 500, described above with reference to FIG. 5. The method 1800 then proceeds to block 1824 where an ionic solution is provided in the fluidic channel. Block 1824 may be substantially similar to block 528 of the method 500, described above with reference to FIG. 5. In embodiments of the method 1800, blocks 1820, 1822, and/or 1824 may be omitted, performed by a different entity, and/or performed outside of a CMOS process.

Thus, the FET 1910 is modified to form the BioFET 2606. The BioFET 2606 allows receptor to control the conductance of the BioFET 2606, while the gate structure 1914 (e.g., polysilicon) provides a back gate. The gate structure 1914 provides a back gate that can control the channel electron distribution without a bulk substrate effect. If the receptors attach to a molecule, the resistance of the field-effect transistor channel in the active region 1908 between the source/drain 1916 is altered. Therefore, the BioFET 2606 may be used to detect one or more specific molecules, including biomolecules or bio-entities, in the environment around and/or in the opening 2302. The BioFET 2606 may be arranged in an array type pattern such as described above with reference to FIGS. 3 and/or 4. The interconnect 2014 may provide a bias to the BioFET 2606 including, for example, to the front gate or receptor/interface layer.

In an embodiment, a CMOS fabrication facility (e.g., foundry) may process the method 500 and/or the associated device up to the fluidic channel formation. In an embodiment, a subsequent user may provide the surface treatment technologies, ionic solutions, receptors, and the like. For example, a foundry may provide a device such as described above with reference to FIGS. 14 and/or 25 to a user (e.g., customer).

In summary, the methods and devices disclosed herein provide a BioFET that is fabricated using CMOS and/or CMOS compatible processes. Some embodiments of the disclosed BioFET may be used in biological and/or medical applications, including those involving liquids, biological entities, and/or reagents. One detection mechanism of some embodiments described herein includes a conductance modulation of the FET of the BioFET due to the binding of the target bio-molecule or bio-entity to the gate structure, or a receptor molecule disposed (e.g., immobilized) on the gate structure of a device.

Some embodiments of the BioFET described herein include an inverted FET, which may be fabricated at least in part using conventional processes. Specifically, a backside of a CMOS FET is opened (e.g., at well gate). A biocompatible interface materials and receptor material are placed in this opening such that the presences of a bio-entity binding can be detected by the change in performance (e.g., current) of the resistor. Thus, in some embodiments, the transistor, includes a source/drain region (e.g., formed as a conventional FET) and a fluidic gate structure including a dielectric film and/or metal stack on top of the dielectric film for biosensing. A passivation layer may protect the newly formed "transistor" from surrounding liquid(s). In some embodiments, the device includes conductive (metal) layers and routings along with inter-layer or inter-metal dielectric circuitry and I/O connections lying underneath the source/drain regions.

Some embodiments of the BioFETs are arranged in an array form. They may include a back-gate for back-gate biasing to improve respond time and/or enhance sensitivity. The gate structures may be built on silicon-on-insulator (SOI) substrates. This may provide advantages in some embodiments of operation at a higher speed and/or consumption of less power. The inverted transistor provided on an SOI substrate may achieve improved fabrication uniformity, have improved process control, and the like. Some embodiments may provide for an improved short-channel effect, for example, due to the formation on a SOI substrate.

In describing one or more of these embodiments, the present disclosure may offer several advantages over prior art devices. In the discussion of the advantages or benefits that follows it should be noted that these benefits and/or results may be present is some embodiments, but are not required. Advantages of some embodiments of the present disclosure include the ability to offer a customer-customizable product. For example, fluidic channel formation, receptor introduction and the like may be performed by a customer. Other examples of embodiments include provision of a bio-friendly interface material. As a further example of advantages of one or more embodiments described herein, in conventional devices it is typical to require high aspect ratio processing to form a bio-compatible interface (e.g., requiring etching from a front surface of the substrate to a gate structure). Because the present methods provide for processing on a backside of a thinned wafer, the aspect ratio may be reduced. The resultant device may be beneficial in that the backside gate can easily control the channel electrode distribution and reduce the bulk substrate effect as it is provided by the gate structure (e.g., polysilicon electrode) rather than the substrate.

Further exemplary advantages of some embodiments include, but are not limited to, separated electrical and fluidic elements, which may be optimized independently without cross-interference. The separated electrical and fluidic elements may also or alternatively minimize an impact of signal attenuation due to parasitic capacitance (e.g., of metal layers). Further exemplary advantages of some embodiments include the ability to select suitable materials for the fluidic gate based on desired design goals, such as, for example, improved association and dissociation capabilities and binding capacity based on a designer's selection of fluidic gate materials (dielectric and/or metal); minimized leakage current due to choices of fluidic gate materials (e.g., dielectric) with larger conduction band offset; enhanced sensitivity due to the designers choice of fluidic gate materials with higher dielectric constant and/or metal conductivity; improved liquid resistance due to the designer's choice of fluidic gate materials; and/or other advantages.

Again it should be understood that any of the advantages above may be present in some embodiments of the disclosure, but are not required of any specific embodiment. Further, it is understood that different embodiments disclosed herein offer different disclosure, and that they may make various changes, substitutions and alterations herein without departing from the spirit and scope of the present disclosure.

Thus, it will be appreciated that in one embodiment a BioFET device is described that includes a substrate and a gate structure disposed on a first surface of the substrate. The device further includes an isolation layer disposed on a second (and opposing) surface of the substrate. The isolation layer includes an opening that has an interface layer formed on the second surface of the substrate in the opening.

In another embodiment, a semiconductor device is provided that includes an array of BioFET devices. The array is connected to at least one sense amplifier. The array of BioFET devices may include a BioFET device having a gate structure as a back gate and an interface layer formed on a channel region of the BioFET device operable to function as a front gate.

As another example, a device including a BioFET device and a sense amplifier coupled to the BioFET device is provided. The BioFET device includes a gate structure formed on a substrate, a source region and a drain region formed in the substrate adjacent the gate structure and a channel region interposing the source and drain regions and underlying the gate structure. An interface layer is disposed on the channel region. The interface layer is disposed on a first surface of the channel region and the gate structure is disposed on the opposing, second surface of the channel region. The interface layer is operable to provide a binding interface for at least one of a biomolecule and a bio-entity. An input/output pad may be disposed on the substrate having the gate structure. Alternatively, an input/output pad is disposed on carrier substrate connected to the substrate. Furthermore, a plurality of lines (e.g., bit lines) may be coupled to BioFET device operable to carry a current when the BioFET detects a target biomolecule or bio-entity.

In yet another embodiment, a method of fabricating a BioFET device includes providing a device substrate having a FET device disposed on the device substrate. A multi-layer interconnect (MLI) is then formed on a first surface of the device substrate. A carrier substrate is attached to the MLI. The carrier substrate may be attached to a passivation layer formed on the MLI. The device substrate is thinned to expose a channel region of the FET device. An isolation layer is formed on a second surface of the thinned device substrate, an opening in the isolation layer exposes the channel region. An interface layer may be formed on the exposed channel region.

In still another embodiment, a method of fabricating a BioFET device includes providing a device substrate having a FET device disposed on the device substrate and forming a multi-layer interconnect (MLI) on a first surface of the device substrate. A carrier substrate is attached to the MLI. The carrier substrate includes at least one conductive line and a bond pad or bonding layer. The device substrate is then thinned to expose a channel region of the FET device. An isolation layer is formed on a second surface of the thinned device substrate, the isolation layer includes an opening to expose the channel region. A portion of the device substrate is removed to expose the bond pad or bonding layer on the carrier substrate.

What is claimed is:

1. A BioFET device, comprising:
    a FET device on a semiconductor substrate, wherein the FET device includes a gate structure formed on a first surface of the semiconductor substrate and a channel region within the semiconductor substrate, wherein the channel region interposes a source region and a drain region in the semiconductor substrate, and wherein the source and drain regions are disposed within a well region in the semiconductor substrate;
    an isolation layer having a top surface, an opposite bottom surface, and an opening and disposed on a second surface of the semiconductor substrate, the second surface of the semiconductor substrate being parallel to and opposing the first surface of the semiconductor substrate, wherein the opening is located over the channel region of the FET device, the channel region including a portion of the second surface of the semiconductor substrate, and wherein the top surface of the isolation layer is a greater distance from the second surface of the semiconductor substrate compared to the bottom surface of the isolation layer;
    an inorganic layer disposed on the channel region of the second surface of the semiconductor substrate in the opening, wherein the inorganic layer has a top surface and an opposite bottom surface, wherein the top surface of the inorganic layer is a greater distance from the second surface of the semiconductor substrate compared to the bottom surface of the inorganic layer, and wherein the top surface of the isolation layer is a greater distance from the second surface of the semiconductor substrate compared to the top surface of the inorganic layer;
    an insulating layer disposed on the isolation layer;
    a fluidic channel disposed on the insulating layer and the isolation layer, wherein the inorganic layer is disposed within a cavity of the fluidic channel; and
    a plurality of biomolecules bound to the inorganic layer.

2. The BioFET device of claim 1, wherein the plurality of biomolecules includes enzymes, oligonucleotides, or monoclonal antibodies.

3. The BioFET device of claim 1, further comprising a multi-layer interconnect (MLI) structure on the first surface of the semiconductor substrate, wherein the MLI structure includes at least a first conductive layer and a second conductive layer interposed by an inter-layer dielectric (ILD) layer.

4. The BioFET device of claim 1, wherein the BioFET device is a first BioFET device, wherein a second BioFET device is connected to the first BioFET device by a first conductive line, wherein a third BioFET device and a fourth BioFET device are connected to a second conductive line, and wherein the first, second, third and fourth BioFET devices are disposed in an array configuration.

5. The BioFET device of claim 4, wherein the first conductive line is configured to carry a current when the first or second BioFET device detects a binding event between a target biomolecule and the plurality of biomolecules on the inorganic layer of the first or second BioFET device, and wherein the second conductive line is configured to carry a current when the third or fourth BioFET device detects a binding event between the target biomolecule and the plurality of biomolecules on the inorganic layer of the third or fourth BioFET device.

6. The BioFET device of claim 1, wherein the inorganic layer comprises a dielectric material and a plurality of deposited layers.

7. The BioFET device of claim 1, wherein an inter-layer dielectric (ILD) layer is disposed on the first surface of the semiconductor substrate and on the well region.

8. The BioFET device of claim 7, wherein a first surface of the well region is in physical contact with the ILD layer and a second surface of the well region is in physical contact with the isolation layer.

9. A BioFET device, comprising:
a FET device on a semiconductor substrate, wherein the FET device includes a gate structure formed on a first surface of the semiconductor substrate and a channel region within the semiconductor substrate, wherein the channel region interposes a source region and a drain region in the semiconductor substrate;
an isolation layer having an opening and disposed on a second surface of the semiconductor substrate, the second surface of the semiconductor substrate being parallel to and opposing the first surface of the semiconductor substrate, wherein the opening is located over the channel region of the FET device, the channel region including a portion of the second surface of the semiconductor substrate;
an interface material on the channel region of the second surface of the semiconductor substrate in the opening;
a multi-layer interconnect (MLI) structure on the first surface of the semiconductor substrate, wherein the MLI structure includes at least a first conductive layer and a second conductive layer interposed by an inter-layer dielectric (ILD) layer;
a trench extending through the isolation layer and through the semiconductor substrate to the first conductive layer of the MLI structure;
an interconnect layer disposed in the trench and making conductive contact with the first conductive layer of the MLI structure;
an insulating layer disposed on the interconnect layer in the trench and on the isolation layer, wherein at least a first portion of the interconnect layer is interposed between the isolation layer and the insulating layer;
a fluidic channel disposed on the insulating layer and the interconnect layer; and
a plurality of biomolecules bound to the interface material.

10. The BioFET device of claim 9, wherein the plurality of biomolecules includes enzymes, oligonucleotides, or monoclonal antibodies.

11. The BioFET device of claim 9, wherein the interconnect layer is configured to provide a surface connection to a wire bond or solder bump.

12. The BioFET device of claim 9, wherein the BioFET device is a first BioFET device, wherein a second BioFET device is connected to the first BioFET device by a first conductive line, wherein a third BioFET device and a fourth BioFET device are connected to a second conductive line, and wherein the first, second, third and fourth BioFET devices are disposed in an array configuration.

13. The BioFET device of claim 12, wherein the first conductive line is configured to carry a current when the first or second BioFET device detects a binding event between a target biomolecule and the plurality of biomolecules on the interface material of the first or second BioFET device, and wherein the second conductive line is configured to carry a current when the third or fourth BioFET device detects a binding event between the target biomolecule and the plurality of biomolecules on the interface material of the third or fourth BioFET device.

14. The BioFET device of claim 9, wherein the interface material comprises a dielectric material and a plurality of deposited layers.

15. The BioFET device of claim 9, wherein at least a second portion of the interconnect layer is interposed between the isolation layer and the fluidic channel.

16. The BioFET device of claim 9, wherein a first portion of the insulating layer is interposed between the fluidic channel and the isolation layer and a second portion of the insulation layer is interposed between the fluidic channel and the interconnect layer.

17. A BioFET device, comprising:
a FET device on a semiconductor substrate, wherein the FET device includes a gate structure formed on a first surface of the semiconductor substrate and a channel region within the semiconductor substrate, wherein the channel region interposes a source region and a drain region in the semiconductor substrate, and wherein the source and drain regions are disposed within a well region in the semiconductor substrate;
an isolation layer having an opening and disposed on a second surface of the semiconductor substrate, the second surface of the semiconductor substrate being parallel to and opposing the first surface of the semiconductor substrate, wherein the opening is located over the channel region of the FET device, the channel region including a portion of the second surface of the semiconductor substrate;
an inorganic layer disposed on the channel region of the second surface of the semiconductor substrate in the opening, the inorganic layer having a lower thickness than the isolation layer;
a multi-layer interconnect (MLI) structure on the first surface of the semiconductor substrate, wherein the MLI structure includes at least a first conductive layer and a second conductive layer interposed by an inter-layer dielectric (ILD) layer;
a carrier substrate coupled to the first conductive layer of the MLI structure;
an insulating layer disposed on the isolation layer;
a fluidic channel disposed on the insulating layer and the isolation layer; and
a plurality of biomolecules bound to the interface material.

18. The BioFET device of claim 17, wherein the plurality of biomolecules includes enzymes, oligonucleotides, or monoclonal antibodies.

19. The BioFET device of claim 17, wherein the carrier substrate includes one or more bonding elements connected to the first conductive layer of the MLI structure.

20. The BioFET device of claim 17, wherein the BioFET device is a first BioFET device, wherein a second BioFET device is connected to the first BioFET device by a first conductive line, wherein a third BioFET device and a fourth BioFET device are connected to a second conductive line, and wherein the first, second, third and fourth BioFET devices are disposed in an array configuration.

* * * * *